(12) United States Patent
Erlich et al.

(10) Patent No.: US 8,407,012 B2
(45) Date of Patent: Mar. 26, 2013

(54) METHODS AND SYSTEMS OF DNA SEQUENCING

(75) Inventors: Yaniv Erlich, Cold Spring Harbor, NY (US); Partha Pratim Mitra, New York, NY (US); Gregory J. Hannon, Huntington, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 748 days.

(21) Appl. No.: 12/498,229

(22) Filed: Jul. 6, 2009

(65) Prior Publication Data

US 2010/0160172 A1 Jun. 24, 2010

Related U.S. Application Data

(60) Provisional application No. 61/078,205, filed on Jul. 3, 2008.

(51) Int. Cl.
*G01N 33/50* (2006.01)
*G06F 15/00* (2006.01)

(52) U.S. Cl. ............................................. 702/20; 712/1

(58) Field of Classification Search ........................ None
See application file for complete search history.

(56) References Cited

U.S. PATENT DOCUMENTS 7,115,400 B1   10/2006   Adessi et al.

OTHER PUBLICATIONS

Chaisson, M. & Pevzner, P. Short read fragment assembly of bacterial genomes. Genome Res 18, 324-330 (2008).
Chang, CC. & Lin, C. LIBSVM : a library for support vector machines. ACM Transactions on Intelligent Systems and Technology, vol. 2, No. 3, pp. 27:1-27:27 (Apr. 2011).
Chi, K. "The year of sequencing,". Nat Methods 5, 11-14 (2008).
Cokus, S. et al. Shotgun bisulphite sequencing of the *Arabidopsis* genome reveals DNA methylation patterning. Nature (5 pages) (2008), vol. 452 pp. 215-219.
Eisen, JA. et al. "Macronuclear Genome Sequence of the Ciliate *Tetrahymena thermophila*, a Model Eukaryote." PLoS Biol 4(9), e286, pp. 1620-1642 (2006).
Hillier, L. et al. Whole-genome sequencing and variant discovery in *C. elegans*. Nat Methods 5, 183-188 (2008).
Kailath, T. & Poor, H.V. Detection of stochastic processes. IEEE Transactions on Information Theory, 44, 2230-2259 (1998).
Kent, W. BLAT—the BLAST-like alignment tool. Genome Res 12, 656-664 (2002).
Korbel, J. et al. Paired-end mapping reveals extensive structural variation in the human genome. Science 318, 420-426 (2007).
Metzker, M. Emerging technologies in DNA sequencing. Genome Res 15, 1767-1776 (2005).
Metzker, M., Raghavachari, R., Burgess, K. & Gibbs, R. Elimination of residual natural nucleotides from 3'-O-modified-dNTP syntheses by enzymatic mop-up. BioTechniques 25, 814-817 (1998).
Pennisi, E. Breakthrough of the year. Human genetic variation. Science 318, 1842-1843 (2007).
Whiteford, N. et al. An analysis of the feasibility of short read sequencing. Nucleic Acids Res. 33, e171, p. 6 pages (2005).
Quinlan et al., "Pyrobayes: an improved base caller for SNP discovery in pyrosequences," Nature Methods, vol. 5, pp. 179-181 (Feb. 2008).

*Primary Examiner* — John S Brusca
(74) *Attorney, Agent, or Firm* — Wilmer Cutler Pickering Hale and Dorr LLP

(57) ABSTRACT

Methods and systems of DNA sequencing that compensate for sources of noise in next-generation DNA sequencers are described.

35 Claims, 14 Drawing Sheets

FIGURE 4
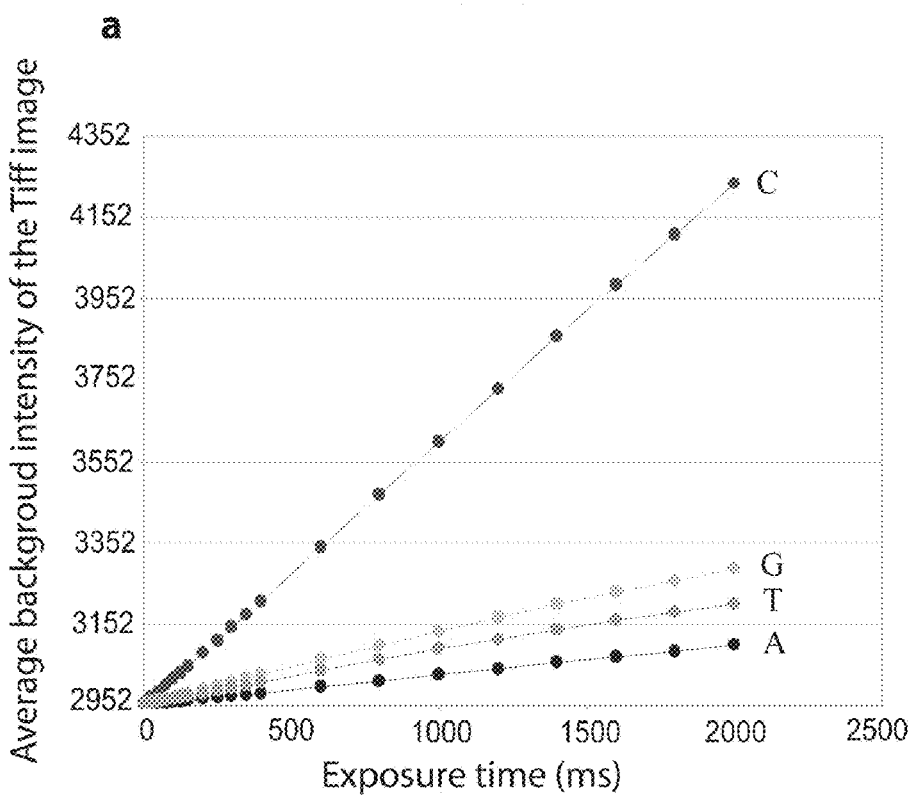
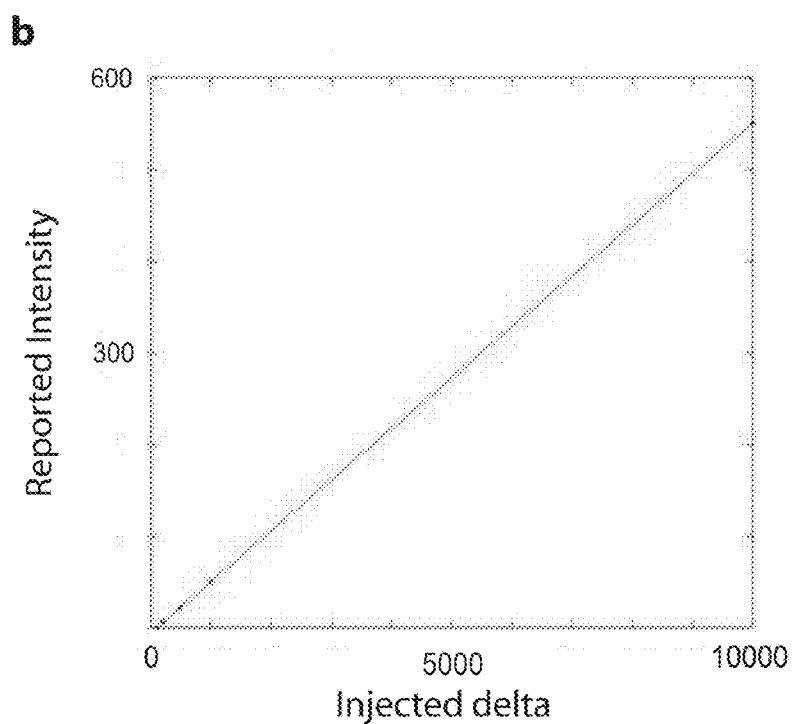

FIGURE 5
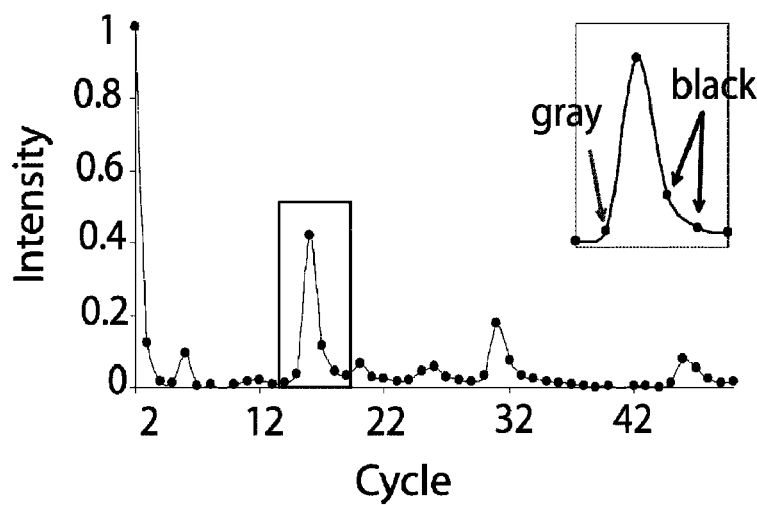
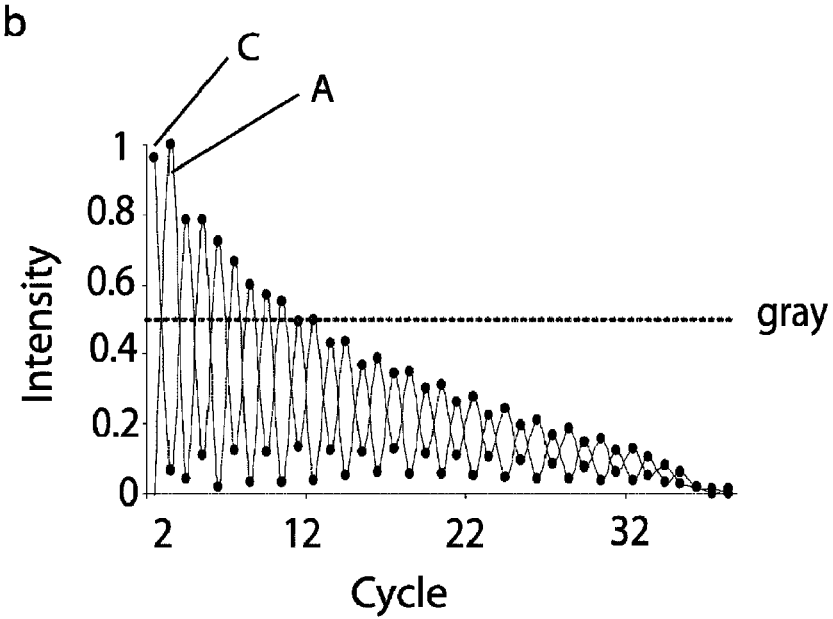

FIGURE 7, CONT.
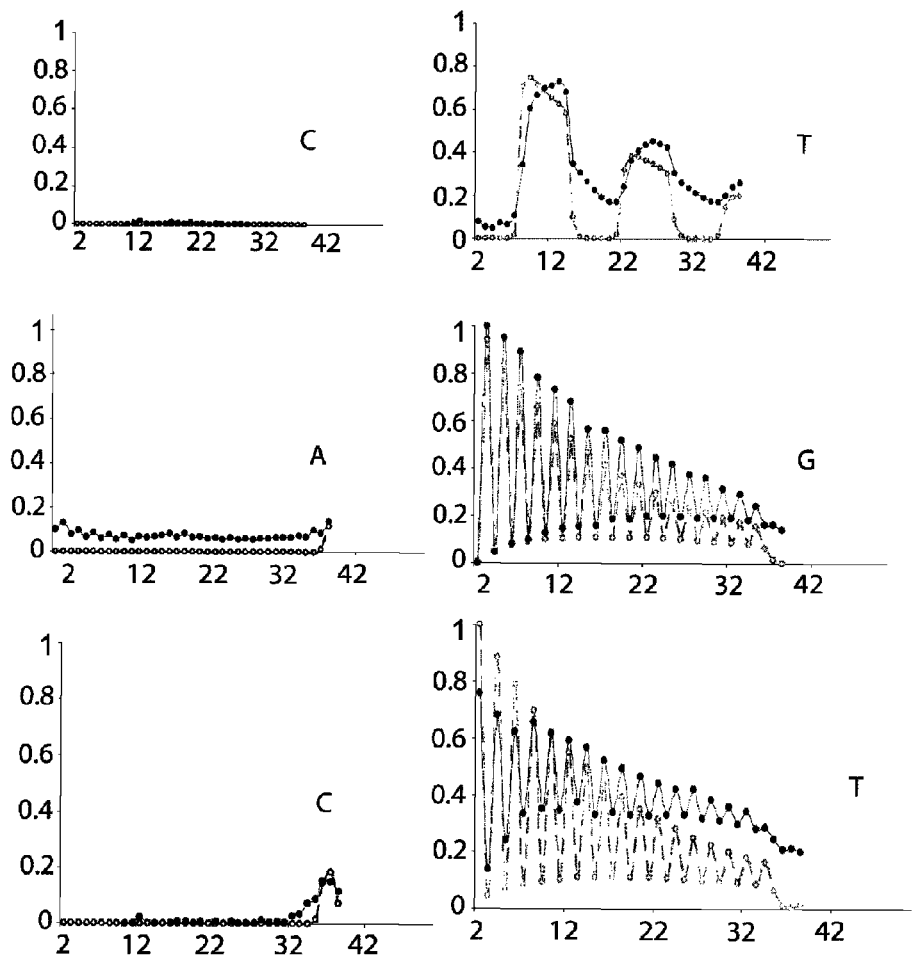

FIGURE 8
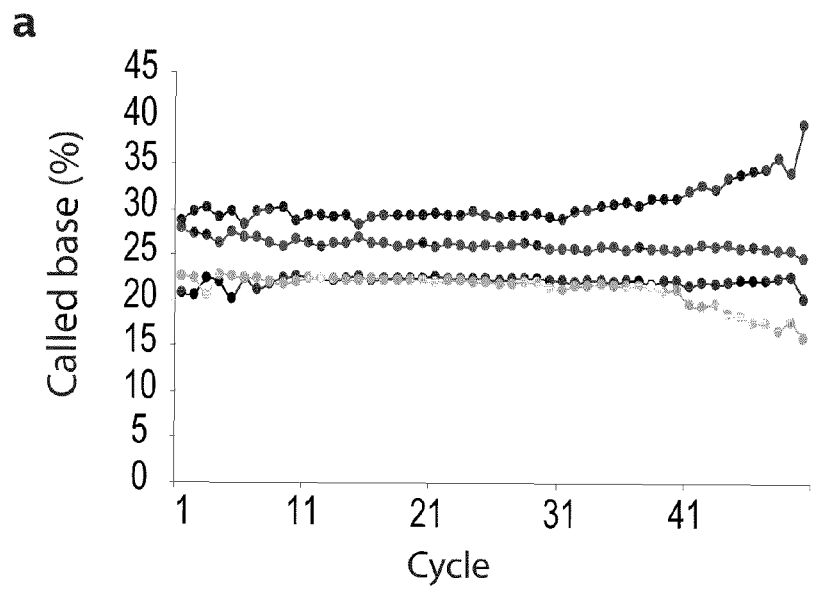
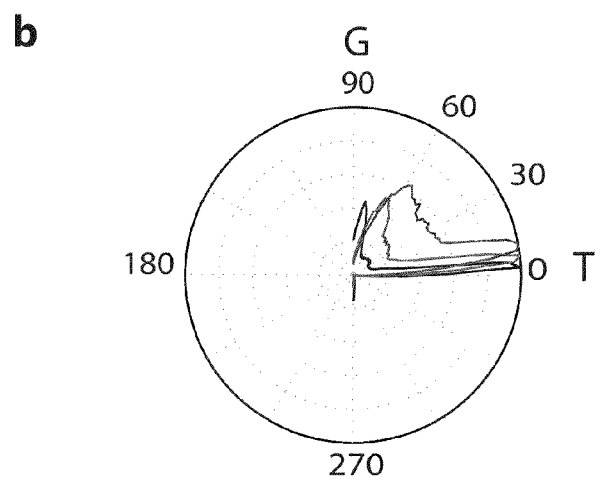
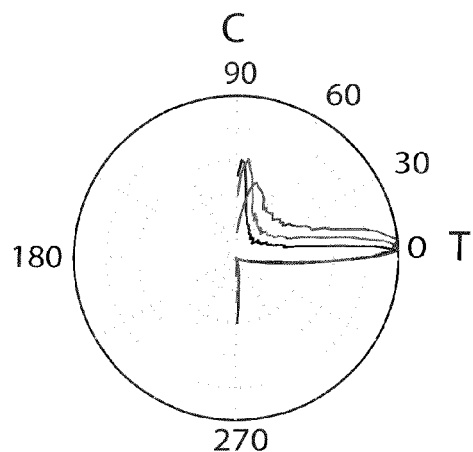

FIGURE 11

|  | 1 .50 |
|---|---|
| Δ on random content | CAGTCGGCCGTCGGTATCCTGGTGGTGGCTAGGCTGTCTCTTTCCACGGC<br>GCAGTAGTGTTGGTTCTGTAGTGGAATGTGCGGTTGTTGAGAATTCAGTA<br>CGCCTTACAATTCAAAGTCCATATAACTTTGAATAACCTTACATCGATAT<br>CTAGCCGCGACAACATAGCAGGCACGAGAGTCGACGGACAGCGGATGCGA |
| Δ on homeo-polymer content | ACAAAAAAAAAAAAACAAAAAAAAAAAAAAACAAAAAAAAAAAAAACAAAAA<br>AGAAAAAAAAAAAAGAAAAAAAAAAAAAAAGAAAAAAAAAAAAAAGAAAAA<br>TCTTTTTTTTTTTTCTTTTTTTTTTTTTTCTTTTTTTTTTTTTTCTTTTT<br>TGTTTTTTTTTTTTGTTTTTTTTTTTTTTGTTTTTTTTTTTTTTGTTTTT |
| MS | ACACACACACACACACACACACACACACACACATTG<br>GTGTGTGTGTGTGTGTGTGTGTGTGTGTGTGTGCCA |
| Θ | AAAAAAACCCCCCCAAAAAAACCCCCCCAAAAAAACCC<br>GGGGGGGTTTTTTTGGGGGGGTTTTTTTGGGGGGGTTT |

FIGURE 12

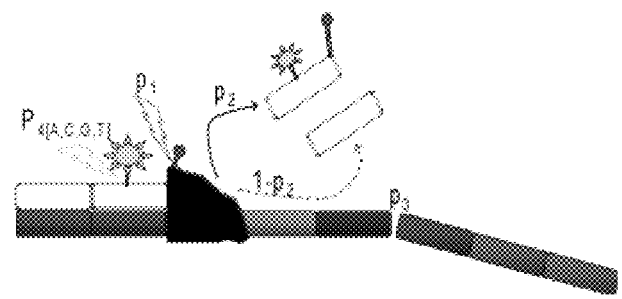

METHODS AND SYSTEMS OF DNA SEQUENCING

This application claims priority to U.S. Provisional Patent Application Ser. No. 61/078,205, filed Jul. 3, 2008, which is hereby incorporated by reference in its entirety.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

Parallel sequencing platforms are revolutionizing biological research[1,2]. They impact many aspects of genomics including studies of sequence and structural variation in genomes[3,4], and studies of the epigenome[5]. Nevertheless, these platforms are error prone and suffer from short read lengths as compared to conventional sequencers[4]. We sought to improve the base calling procedure for sequencers such as the Illumina® Genome Analyzer (GA) manufactured by Illumina (San Diego, Calif.) in order to obtain more accurate and longer sequence reads. Such an improvement would boost overall output per run, increasing genomic coverage and the ability to detect sequence variants. Longer reads also increase mapping precision[6] and enhance de-novo genome assembly[7].

SUMMARY OF THE INVENTION

Parallel sequencing platforms are capable of simultaneous sequencing a plurality of DNA fragments. These platforms, dubbed next generation sequencing or high throughput sequencing, are characterized by high error rates, as compared to the legacy conventional sequencing platforms. However, a major advantage of the parallel sequencing is the ability to learn the noise pattern and other distortion parameters by observing the signals of a small known subset of DNA fragments. The invention provides methods for improvements in sequence determination of these platforms using machine learning approach, which is trained according to the known subset and then decodes signals obtained from the unknown fragments. For example, this method improves in the sequence determination using Solexa sequencing technology on the Illumina Genome Analyzer. (See U.S. Pat. No. 7,115,400, Solexa Ltd., directed to Methods of Nucleic Acid Amplification and Sequencing). Embodiments provide a systematic analysis of the sources of noise in the Illumina Genome Analyzer that cause error rates to climb with cycle number. Some embodiments provide that noise factors include de-synchronization of polymerases (phasing), progressive loss of signal (fading), and cycle-depending increases in the fluorescent cross-talk among individual nucleotides due to insufficient fluorophore cleavage. Embodiments provide a novel base-calling strategy and base caller, termed Alta-Cyclic, that allows for compensation of these noise sources and is based on a machine learning approach. This base caller allows valuable long base reads, enhances the number of accurate reads as compared to standard software, and reduces systematic biases that degrade the ability to confidently identify sequence variants. Although the analysis exemplified herein relates to the Illumina platform, the strategies and methods described herein are also be applicable to other parallel sequencing platforms.

BRIEF DESCRIPTION OF THE FIGURES

FIG. 4|Illumina image processing is linear. (a) The optic chain is linear. A series of images with different exposure times were taken from an intact flow cell, and the background intensity was measured for all the channels (A—blue, C—red, G—yellow, T—green). The linear relationship between the input and the output indicates a linear optic chain. (b) Illumina's Firecrest image analysis module applies a linear transformation to the image. Artificial TIFF images were created with constant background and a few brighter pixels (spatial delta functions) with different brightness levels. The images were processed by Firecrest and the reported intensities were compared to the input pixels. Again, the linear relationships between the input and output indicate linear processing.

FIG. 5|Output of the impulse response test. (a) Shown are the averaged intensities of the cytosine channel from DNA clusters with delta function sequence: GCAGTAGTGTTG-GTTCTGTAGTGGAATGTGCGGTTGTTGAGAATTCA-GTA (SEQ ID NO: 1) (the first cycle is not shown), after cross-talk correction and normalization. Phasing appears as an anticipation signal that precedes the position of the C in the sequence (gray arrow) and persists in subsequent cycles (black arrows). The diffusive properties of the phasing are shown by relative increase in the residual signal in adjacent cycles to the actual C position. (b) Signal decay (fading) is reflected in intensity reads from microsatellite sequences. Shown are the average intensities of the cytosine (red) and adenine (blue) channels from DNA clusters with the microsatellite sequence ACAC . . . (the first cycle is not shown) after cross-talk correction and normalization. In the absence of fading the signals should converge to half of their initial intensities (gray line). Nevertheless, the signal exponentially decays toward zero, which indicates material loss or another mechanism that gradually disrupts the signal.

FIG. 8|Cross-talk matrix changes explain the anomaly. (a) The percentage of called bases in the phi-X library is plotted as a function of cycle number using the Illumina base caller (A—blue, C—red, G—green, T—purple). The T and the G calls have strong opposite trends. A more moderate opposite trend is observed between the C and A calls. (b) Polar histograms present the ratio between channel intensities correlated with the base preference. The upper polar histogram exhibits the ratios between the G and the T channel. A strong G signal with a weak T one will appear in the bins that are close to 90 degrees and the opposite will appear close to zero degrees. In the first cycle (black) the two lobes are orthogonal which indicates correct cross-talk correction. In later cycles (green and red) the G lobe starts to migrate toward the T lobe, which indicates a change in the cross-talk matrix. In contrast, the polar histogram of the ratio between the C and T channels does not exhibit any major cross-talk change. The size of the lobes is increased because of phasing. In both histograms the main peak for each cycle was normalized to value of 1 for clarity.

FIG. 11|Table showing the sequences of the controlled input set. Twelve DNA fragments were synthesized and used as sequencing templates for determination and validation of the noise model. The first four sequences are delta function sequences on a random context (SEQ ID NOS 3, 1, 4 and 5, respectively, in order of appearance). The second group contains delta function sequences on a homopolymer context (SEQ ID NOS 6-9, respectively, in order of appearance). The positions of the delta function are underlined. The third set comprises dinucleotide microsatellite sequences (MS) (SEQ ID NOS 10-11, respectively, in order of appearance) and the last contains the theta function sequences (SEQ ID NOS 12-13, respectively, in order of appearance).

FIG. 12|Generative Random Walk Model for Signal Distortion in Illumina Sequencing. This schematic representation is similar to FIG. 6, but also includes the probability of insufficient fluorophore cleavage. This probability is unique for each nucleotide and represent by a vector of dimension 4. The differences between the probabilities are responsible for the bias towards calls of a specific nucleotide. The yellow star sign represents a fluorophore. The parameters corresponding to the cross talk matrix are not shown.

DETAILED DESCRIPTION

Figure 1:
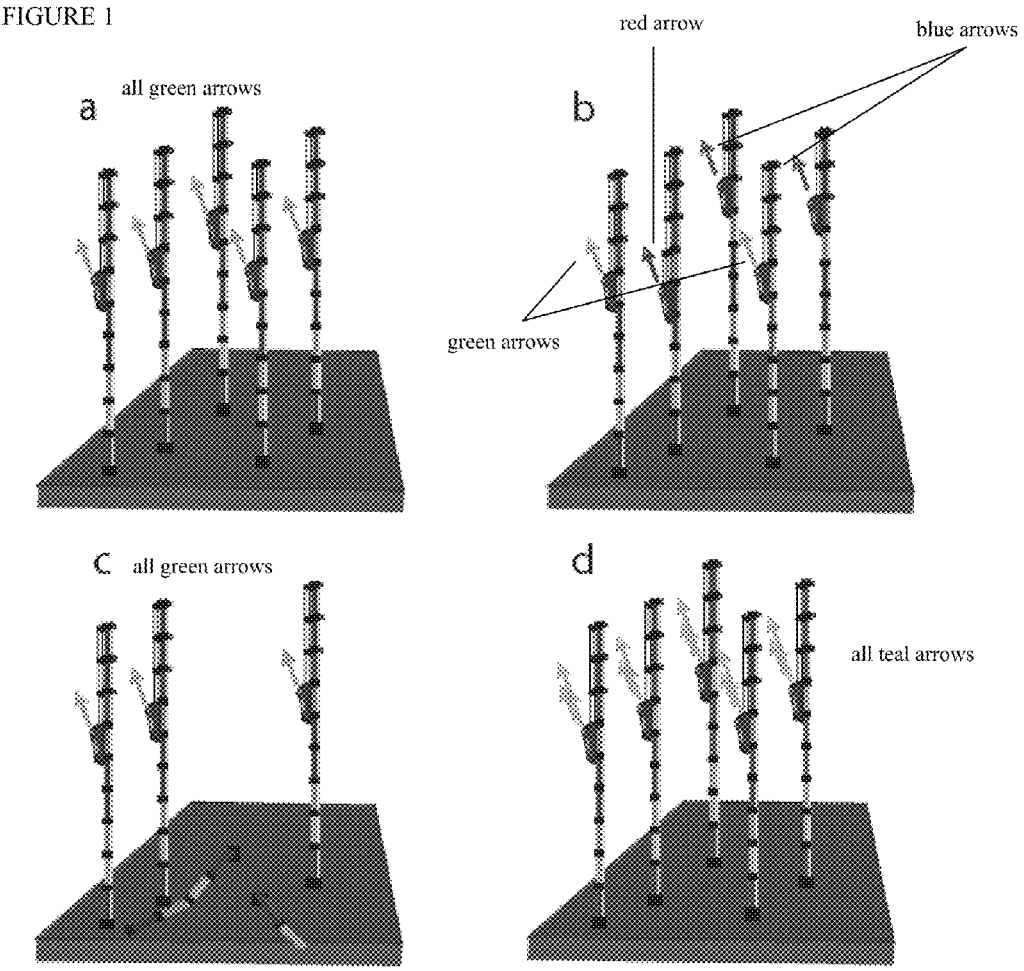
FIG. 1|Schematic representation of main Illumina noise factors. (a, b, c, d) A DNA cluster is comprised of identical DNA templates (colored rods) that are attached to the flow cell. Nascent strands (black boxes) and DNA polymerase (black ovals) are depicted. (a) The ideal situation after several cycles. The signal (green arrows) is strong, coherent, and corresponds to the interrogated position. (b) Phasing noise introduces lagging (blue arrows) and leading (red arrow) nascent strands, which transmit a mixture of signals. (c) Fading is attributed to lose of material that reduces the signal intensity. (d) Changes in the fluorophore cross-talk cause misinterpretation of the received signal (teal arrows). (b, c, d) For simplicity the noise factors are presented separately from each other.

This application relates to a base-calling algorithm and implementation using supervised learning to enhance DNA sequencing in high throughput sequencing platforms. The algorithm has two steps—training and calling. In the training step, the algorithm infers parameters that describe the distortion and the noise pattern of the sequencing operation from known exemplars (also referred to as a distortion function), and in the calling step it uses the inferred parameters to enhance the quality of base-calling of unknown libraries.

The training step is based on a training library, which comprises nucleic acid molecules of known or mostly known sequences. The training library can be derived from a previously sequenced genome, such as the phi-X bacteriophage genome, or it can be a synthetic library. This library is simultaneously sequenced with the other libraries, and is used to create the training set—portions of the reference genome and the corresponding signals from the sequencer. The training set serves as an input for the training step.

In order to infer the model parameters, the algorithm tracks the discrepancies between the expected signals of the known sequences and the actual signals, and it optimizes the parameters to fit the discrepancies. The optimization procedure itself can be done using various well-known methods such as exhaustive search, beam search or quadratic programming. The underlining assumption is that the error profile of the training set is similar to the other DNA libraries in the run. Thus, the inferred parameters can be used to deconvolute the noise of the other libraries.

After the parameters are tuned, the algorithm enters to the calling step in which it deconvolutes the noise from the signals of the other libraries. The enhanced signals are decoded and more accurate sequences are obtained.

The invention is directed to an improvement to sequencing methods whereby parallel DNA fragments are sequenced simultaneously. This invention provides for improvements in sequence determination from the Illumina Genome Analyzer (Solexa) instrument. The invention provides for systematic analysis of sources of noise that cause error rates to climb with cycle number. The invention provides that de-synchronization of polymerases (phasing), progressive loss of signal (fading) and cycle-depending increases in the fluorescent crosstalk among individual nucleotides due to insufficient fluorophore cleavage. Embodiments provide for a computer-implemented method of base-calling, termed herein Alta-Cyclic, that allows compensation of these noise sources and is based on machine learning approach. This allows valuable 78-base reads, enhances the number of accurate reads by several folds, and reduces systematic biases that degrade the ability to confidently identify sequence variants. Though the exemplary analysis provided in the examples is related to the Illumina platform, the general strategies as provided by the invention may also be applicable to other next generation-platforms. Alta-Cyclic is available on hannonlab.cshl.edu/Alta-Cyclic/main.html.

In one embodiment, a computer-implemented method of DNA sequencing is provided, which includes: (a) providing a training library of DNA fragments, the DNA sequence of each fragment in the training library being substantially known; (b) providing a DNA sample to be sequenced; (c) measuring in parallel a first signal and a second signal, the first signal corresponding to a nucleotide in the DNA fragments from the training library, the second signal corresponding to a nucleotide in the DNA sample; (d) determining a distortion function, the distortion function representing a difference between the first signal and an expected value of the first signal, the expected value of the first signal being based on the training library; and (e) applying the distortion function to the second signal to generate the sequence of the DNA sample.

The distortion function can include a parameter representing a source of noise in the sequencer. The distortion function can be determined by a learning machine, which learning machine can be a support vector machine. The learning machine can be cross-validated, wherein a first signal corresponding to a nucleotide in the DNA fragments from a fraction of the training library is measured and used to determine the distortion function as described above, and a second fraction of the training library is used to cross-validate the learning machine. In some embodiments, a grid search is performed for the at least one parameter describing a source of noise in the sequencer using results of the cross-validating. Applying the distortion function can include deconvoluting the second signal.

In one embodiment, a computer-implemented method is provided for determining the nucleotide sequence of a nucleic acid molecule (such as DNA, or RNA), including: (a) generating, for each sequencing run, a training set using a training library, wherein the training library comprises a plurality of DNA fragments and their known sequences; (b) providing an algorithm based on machine learning, wherein the algorithm is trained using the training set and at least one learning machine; (c) providing a DNA sample to be sequenced; (d) measuring at least one intensity signal that corresponds to a nucleotide in the DNA sample and optionally deconvoluting the at least one intensity signal; and (e) determining at least one sequence for the DNA sample using the at least one intensity signal and the algorithm.

In one embodiment, the training library includes at least about 100 DNA fragments. In another embodiment, the training library includes at least about 1000 DNA fragments. In a further embodiment the training library comprises at least about 10,000 DNA fragments.

In one embodiment, generating the training set includes: (i) measuring at least one intensity signal that corresponds to a nucleotide in the training library DNA; (ii) determining at least one sequence for the training library DNA using the at least one intensity signal and a standard base caller; (iii) aligning the at least one sequence for the training library DNA to its known sequence, thus generating a training set comprising at least one intensity signal measured for the training library DNA and its corresponding correct nucleotide. In one embodiment, the at least one learning machine is a support vector machine In another embodiment, the DNA sequencing is by synthesis, and the algorithm is based on a parametric model, or the first signal and the expected value of the first signal are calculated using a parametric model, wherein the parametric model is given by:

$$R(t, n) = e^{-p_3 t} \int_{-\pi}^{\pi} \left[ 1 - p_1 + \frac{p_1 p_2 e^{i\omega}}{1 - (1 - p_2) e^{i\omega}} \right]^t e^{-i\omega n} \frac{d\omega}{2\pi}$$

wherein
p1 is a probability for block removal that permits further polymerization in a synthesis cycle,
p2 is a probability of incorporation of a blocked nucleotide,
p3 is a probability of strand loss, R is a matrix representing a probability of a nascent strand to be n nucleotides long after t cycles,

D×P=R,

D is a T-by-T diagonal matrix representing exponential decay of the intensity signal, where T is a total number of synthesis cycles, P is a T-by-N matrix representing phasing, where P(t,n) corresponds to a probability of finding a nascent strand with a length n after t synthesis cycles, and N is a length of the longest nascent strand, and cannot be greater than the template length.

In an aspect of the invention, the method further includes determining p1 and p2 using a first grid search. In another aspect of the invention, the method further includes determining optimal learning machine parameters using a second grid search. In another aspect, the invention provides a method wherein a signal I from a j-th DNA cluster ($I_j$) is given by:

$$(\eta_j \cdot D \times P \times S_j) \times G^*(t) = I_j$$

wherein $\eta_j$ is a scalar that represents a size of the j-th DNA cluster,

D is a T-by-T diagonal matrix representing exponential decay of the intensity signal, where T is a total number of synthesis cycles, P is a T-by-N matrix representing phasing, where P(t,n) corresponds to a probability of finding a nascent strand with a length n after t synthesis cycles, N is a length of the longest nascent strand, and cannot be greater than the template length, $S_j$ is an N-by-4 matrix that contains a binary representation of the DNA sequence of the j-th DNA cluster, G is 4-by-4 matrix that represents cross-talk between channels and is dependent on cycle number,

* indicates transposition, and $I_j$ represents the intensity signal from the j-th cluster and is a T-by-4 matrix. The signal can be an intensity signal.

The invention further provides for a method, which further includes deconvoluting the at least one intensity signal using p1 and p2 determined from the first grid search, wherein the deconvoluting comprises performing an inverse transformation given by:

$$(\eta_j \cdot (\hat{P} \times \hat{D})^+ \times D \times P \times S_j) \times G^*(t) \times \hat{G}(t)^{*-1} = (\hat{P} \times \hat{D})^+ \times I_j \times \hat{G}(t)^{*-1}$$

wherein

+ represents pseudo-inverse, $\eta_j \cdot \Sigma \times S_j = Y$, wherein Y is the right hand part of the inverse transformation equation and $\Sigma$ is a band diagonal matrix, D is a T-by-T diagonal matrix representing exponential decay of the intensity signal, where T is a total number of synthesis cycles, P is a T-by-N matrix representing phasing, where P(t,n) corresponds to a probability of finding a nascent strand with a length n after t synthesis cycles, N is a length of the longest nascent strand, and cannot be greater than the template length, $S_j$ is an N-by-4 matrix that contains a binary representation of the DNA sequence of the j-th DNA cluster, G is 4-by-4 matrix that represents cross-talk between channels and is dependent on cycle number,

* indicates transposition, and $I_j$ represents the intensity signal from the j-th cluster and is a T-by-4 matrix.

In another aspect, the invention provides for a method wherein the DNA fragments correspond to or are from a known genome, meaning a genome that has been sequenced. In another embodiment, the DNA fragments include or comprise artificially created or synthetic sequences.

The invention also provides for a computer-implemented method for determining the nucleotide sequence of a given nucleic acid molecule (such as DNA or RNA) using polymerase-based synthesis, including: (a) providing a DNA sample to be sequenced; (b) measuring at least one intensity signal that corresponds to a nucleotide in the DNA sample; and (c) determining at least one nucleotide sequence for the DNA sample using the intensity signal and a correction for cross-talk noise in the intensity signal, wherein the correction for cross-talk noise is dependent upon synthesis cycle number.

The invention also provides for a computer-implemented method for determining the nucleotide sequence of a nucleic acid (e.g., DNA or RNA), using synthesis, for example, polymerase-based synthesis, wherein the method includes: (a) measuring at least one signal that corresponds to a nucleotide in a DNA sample to be sequenced; (b) deconvoluting the at least one signal by an inverse transformation given by:

$$(\eta_j \cdot (\hat{P} \times \hat{D})^+ \times D \times P \times S_j) \times G^*(t) \times \hat{G}(t)^{*-1} = (\hat{P} \times \hat{D})^+ \times I_j \times \hat{G}(t)^{*-1}$$

+ represents pseudo-inverse, $\eta_j \cdot \Sigma \times S_j = Y$, wherein Y is the right hand part of the inverse transformation equation and $\Sigma$ is a band diagonal matrix, D is a T-by-T diagonal matrix representing exponential decay of the intensity signal, where T is a total number of synthesis cycles, P is a T-by-N matrix representing phasing, where P(t,n) corresponds to a probability of finding a nascent strand with a length n after t synthesis cycles, N is a length of the longest nascent strand, and cannot be greater than the template length, $S_j$ is an N-by-4 matrix that contains a binary representation of the DNA sequence of the j-th DNA cluster, G is 4-by-4 matrix that represents cross-talk between channels and is dependent on cycle number,

* indicates transposition, and $I_j$ represents the intensity signal from the j-th cluster and is a T-by-4 matrix; and (c) determining at least one sequence for the DNA sample using the deconvoluted signal. The signal can be, for example, an intensity signal.

The invention also provides computer-implemented method for determining the nucleotide sequence of a nucleic acid molecule (e.g., DNA or RNA), wherein the method includes (a) generating, for each sequencing run on a sequencer, a training set using a first fraction of a training library, wherein the training library comprises a plurality of DNA fragments and their known sequences; (b) providing an algorithm based on machine learning, wherein the algorithm is trained using the training set and at least one learning machine, and wherein the algorithm comprises at least one parameter describing a source of noise in the sequencer; (c) cross-validating the at least one learning machine using a second fraction of the training library; (d) providing a DNA sample to be sequenced; (e) measuring at least one intensity signal that corresponds to a nucleotide in the DNA sample and optionally deconvoluting the at least one intensity signal; and (f) determining at least one sequence for the DNA sample using the at least one intensity signal and the algorithm. In one embodiment, the method further includes performing a grid search for the at least one parameter describing a source of noise in the sequencer using results of the cross-validating.

Further provided is a computer-implemented method for generating a training set to be used in DNA sequencing, including: a) providing a training library, stored in a computer readable medium, wherein the training library comprises a plurality of DNA fragments and their known sequences; b) measuring at least one signal in a DNA sample to be analyzed, wherein the at least one signal corresponds to a nucleotide in the training library DNA; c) determining at least one sequence for the training library DNA using the at least one signal and a standard base caller; d) aligning the at least one sequence for the training library DNA to its known sequence, thus generating a training set comprising at least one signal measured for the training library DNA and its corresponding correct nucleotide.

Additionally provided is a computer-implemented method of DNA sequencing, which method includes: (a) providing a training library of DNA fragments, the DNA sequence of each fragment in the training library being substantially known; (b) generating a set of expected signals, each of the expected signals representing an output expected to be generated by a DNA sequencer when a fragment in the training library is applied to the DNA sequencer; (c) providing a DNA sample to be sequenced; (d) applying the DNA sample and at least some fragments from the training library to the DNA sequencer, the DNA sequencer generating a first signal and one or more control signals, the first signal being indicative of the DNA sequence of the sample, each of the control signals being indicative of the DNA sequence of one of the at least some fragments from the training library; (e) determining a distortion function, the distortion function representing a difference between at least some of the control signals and at least some of the expected signals; (f) applying the distortion function to the first signal to generate an output signal representative of the sequence of the DNA sample.

Also provided is a computer-implemented method of enhancing DNA sequencing outcomes, the method including: a) measuring at least one signal that corresponds to a nucleotide in a DNA sample to be sequenced; b) determining at least one sequence for the DNA sample using the at least one signal and a correction for cross-talk noise in the at least one signal, wherein the correction for cross-talk noise is dependent on a synthesis cycle number; c) inferring parameters that describe the at least one signal by optimizing an objective function that is built upon known exemplars; and d) using the inferred parameters to reduce noise and distortion in the at least one signal, thereby enhancing DNA sequencing outcomes. The objective function can be optimized by any means known to one of ordinary skill in the art. For example, optimizing can be by beam search, branch and bound, exhaustive search, semi-definite programming, or simulated annealing.

The invention includes a system for DNA sequencing including: (i) a training library of DNA fragments, stored on a computer readable medium, the DNA sequence of each fragment in the training library being substantially known; (ii) a DNA sample to be sequenced; (iii) a first signal and a second signal, measured in parallel, the first signal corresponding to a nucleotide in the DNA fragments from the training library, the second signal corresponding to a nucleotide in the DNA sample; and (iv) logic, stored in a computer readable medium, configured (1) to determine a distortion function, the distortion function representing a difference between the first signal and an expected value of the first signal, the expected value of the first signal being based on the training library; and (2) to apply the distortion function to the second signal to generate the sequence of the DNA sample.

The logic can be configured to deconvolute the signal, and the logic can be based on a parametric model given by:

$$R(t, n) = e^{-p_3 t} \int_{-\pi}^{\pi} \left[ 1 - p_1 + \frac{p_1 p_2 e^{i\omega}}{1 - (1 - p_2) e^{i\omega}} \right]^t e^{-i\omega n} \frac{d\omega}{2\pi}$$

wherein
p1 is a probability for block removal that permits further polymerization in a synthesis cycle,
p2 is a probability of incorporation of a blocked nucleotide,
p3 is a probability of strand loss,
R is a matrix representing a probability of a nascent strand to be n nucleotides long after t cycles,
D×P=R,
D is a T-by-T diagonal matrix representing exponential decay of the signal, where T is a total number of synthesis cycles,
P is a T-by-N matrix representing phasing, where P(t,n) corresponds to a probability of finding a nascent strand with a length n after t synthesis cycles, and
N is a length of the longest nascent strand, and cannot be greater than the template length.

In one embodiment, a system for generating a training set to be used in nucleic acid sequencing is provided. The system can include: i) a nucleic acid sample to be analyzed, such as a DNA or RNA, wherein the nucleic acid sample has at least one signal; ii) a training library, stored in a computer readable medium, wherein the training library comprises a plurality of nucleic acid fragments and their known sequences and the at least one signal in the nucleic acid sample that corresponds to a nucleotide in the training library nucleic acids; and iii) logic comprising a set of instructions stored in a computer readable medium and configured to determine at least one sequence for the training library nucleic acid fragments using the at least one signal and a standard base caller and align the at least one sequence for the training library nucleic acid to its known sequence, thus generating a training set comprising at least one signal measured for the training library nucleic acid and its corresponding correct nucleotide.

In another embodiment, the invention provides for method of using a reference genome to generate calibration data to adjust the base calling algorithm. In one aspect, the reference genome in question includes a viral genome, and was used to tune the parameters in the forward model and to fit the learning machine that did the base calling. In chip-based expression assays (e.g., Affymetrix type assays) or in other array platforms, it is known to use some short reference sequences (about 10), but these are small in number and do not play the same role in calibrating the entire "reading" or "calling" algorithm as described herein. What differentiates the usage of a viral genome as a calibration technique as used herein is that the viral genome automatically generates a large variety of short training sequences that will be difficult to generate artificially. Embodiments provide a method where a similarly large number of short sequences (millions) are artificially created and used in the calibration step. The disclosed method is adaptive. However, in one aspect, the calibration data is needed for every run, but this acceptable given that one obtains longer and more correct sequence data (reads). Length is the key in that it is an important aspect of these sequence methods. Long reads are contingent on using an adaptive method.

Embodiments also provide for a methods which include a parametrized forward model (sequences->intensities) that captures the physics of the process and improves base calling.

Illumina/Solexa use a Monte Carlo-based method. In contrast, in the embodiments described herein, the data is premultiplied by the inverse of this forward model before the base calling algorithm is applied; this is a deconvolution step.

Embodiments further provide for methods that comprise usage of a machine learning approach for the final base caller. A support vector model based learning machine is used; other learning machines could also be used. A distinction of the invention is that the methods comprise use of a large training data set and the methods can use a learning machine with a large number of effective degrees of freedom. By contrast, the current Solexa/Illumina pipeline uses a mixture of Gaussians, which has a small number of parameters and is therefore significantly less data adaptive. Thus, a feature of the invention is the highly adaptive nature of the base caller. The methods provided herein can include training the base caller using pilot data generated using a rich training set (for example, a whole viral genome, or a large plurality of DNA fragments with known sequence). In other methods, pilots or "spike in" samples are much more limited in use. This extensive training, as included in the methods of the invention, has to be done for each run of the machine—indicating that there is adaptation to specific details of the run. Currently, the Solexa/Illumina caller does not do this, nor do any of the other "sequencing by synthesis" methods.

In order to improve next-generation sequencer base calling, we dissected the main sources of noise within the sequencer and constructed a parametric model describing phasing by a random walk process as well as other sources of signal distortion. Based on this improved understanding of noise sources, we created a novel base caller algorithm, called Alta-Cyclic. The algorithm learns the noise characteristics of each run and finds the optimal criteria for accurately calling bases. Alta-Cyclic improves dramatically the sequencing accuracy both on GAI and GAII machines, and enhances the valuable sequencing length. Though the analysis disclosed herein relates to the Illumina platform, the general strategies described can also be applicable to other next generation-platforms.

The invention provides for analysis of the sequencing platform's non-stationary noise factors, as these accumulate throughout the run and reduce accuracy in later cycles. The invention provides the determination that three noise factors dominate (FIG. 1). The first one is phasing, which is a source of noise in sequencers that utilize cyclic-reversible termination (CRT)[8,9], like the Illumina platform. Briefly, CRT involves repetitive cycles of three steps: (a) extension of a nascent nucleic acid strand with addition of a single blocked and fluorophore-labeled nucleotide (b) imaging (c) block and fluorophore removal in preparation for the next synthesis cycle. In the idealized situation (FIG. 1a), after any number of cycles, the lengths of all nascent strands within the DNA cluster would be the same and in correspondence with the interrogated position. This would generate a strong coherent signal. Nevertheless, imperfections in the chemistry of CRT cause stochastic failures in incorporation or block removal, or incorporation of more than one nucleotide in a particular cycle. These create variation in nascent strand lengths, introducing lagging (too short) and leading (too long) nascent strands within the cluster. This variation reduces the purity of signal output from the interrogated position by contamination with signals from adjacent nucleotides, which is referred as phasing noise (FIG. 1b). The nascent strand length variation increases with every cycle and consequently the precision of base calling drops, this limits maximal useful read lengths. The second dominant noise factor is fading (FIG. 1c)—an exponential decay in fluorescent signal intensity as a function of cycle number. This is likely attributable to material loss during sequencing. The third non-stationary noise factor is a cycle-dependent change in fluorophore cross talk (FIG. 1d), which induces a substantial bias toward certain base calls in later cycles. The physical basis of this observation is insufficient fluorophore cleavage from the nucleotides. Since nucleotide-fluorophore combinations have different cleavage efficiencies and found in different frequencies in the sequenced library, residual signals are building up in corresponding rates and modulate the cross-talk. Taking into account these three noise factors, the method provides for the construction and testing of a parametric model that describes signal distortion as function of cycle. The model provided by the invention suggests that accounting for both phasing and changes in the cross-talk matrix, enhances the signal-to-noise ratio and improves the quality of sequence reads.

Figure 2:
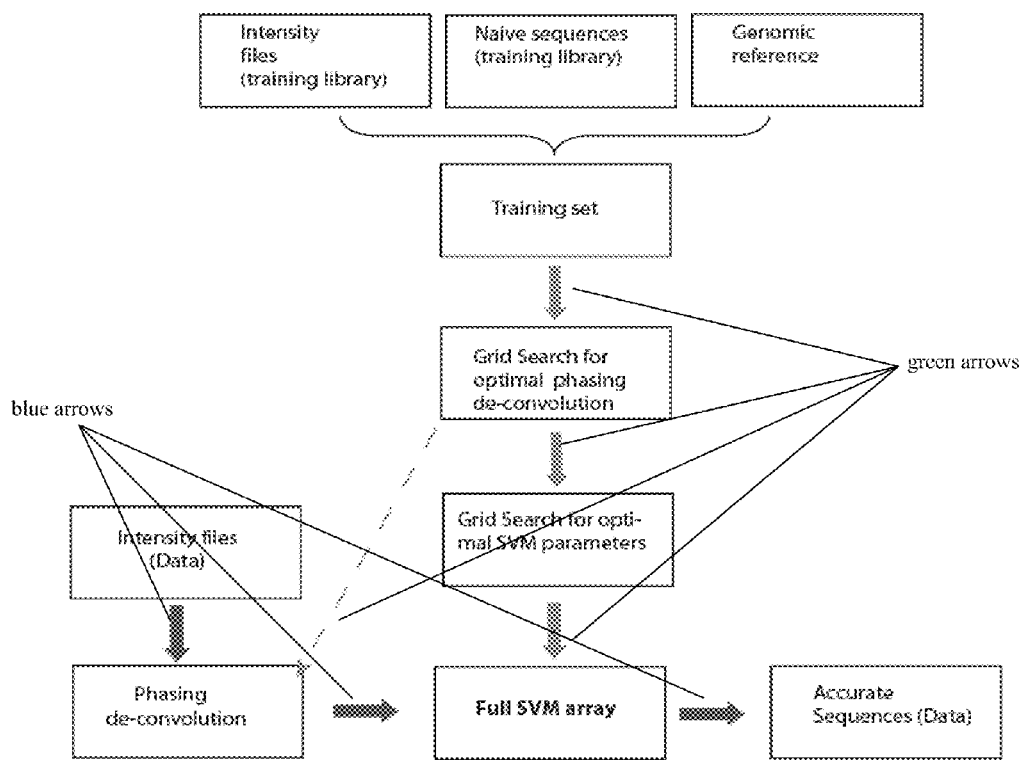
FIG. 2|Alta-Cyclic base caller data flow. The training process (green arrows) starts with creation of the training set by linking intensity reads and a corresponding genome sequence. Then, two grid searches are used to optimize the parameters to call the bases. After optimization, a final SVM array is created, each of which corresponds to a cycle. In the base calling stage (blue arrows), the intensity files of the desired library undergo de-convolution to correct for phasing noise using the optimized values, and sent for classification with the SVM array. The output is processed, and sequences and quality scores are reported.

Based upon this analysis, the invention further provides for a novel base caller, named Alta-Cyclic, which is designed to specifically address these noise factors (FIG. 2). Alta-Cyclic works in two stages: the training stage and the base calling stage. During the training stage, Alta-Cyclic learns run-specific noise patterns according to the model and finds an optimized solution that reduces the effect of these noise sources, i.e., a distortion function. The optimization is mainly achieved by supervised learning using a rich DNA library with a known reference genome. The training library can be derived from a previously sequenced genome, such as the phi-X bacteriophage genome, or it can be a synthetic library. It is preferred that more than 98% of the alignable DNA molecules of the training library will have an accurate reference. Alta-Cyclic then enters the base calling stage and reports all the sequences from the run with the optimized parameters. In some embodiments, signal measurements from the reference genome and the new DNA material can occur simultaneously. Then, the distortion function can be calculated based on the signal noise and other parameters and applied to the signal from the new DNA material. In other embodiments, the signal of the reference genome and the corresponding distortion function can be obtained first, then a signal from a DNA sample can be measured and the distortion function can be applied to the signal from the DNA sample. From the user perspective, Alta-Cyclic mainly operates on the fluorescent intensity values that are generated by Firecrest, the Illumina image processing software. The training process is transparent, although computationally intensive. The main requirement is that one sample on each run have an available reference genome. While the phi-X genome is often used, a common Illumina control, theoretically, any sample can be used provided that there is a corresponding reference. The training library, but not other lanes, should be called using standard base-calling software such as Bustard, the Illumina base-calling software. Both the original intensity data and the reference sequences mapped to the genome following standard base calling are supplied to train Alta-Cyclic. Once trained, Alta-Cyclic base calls all samples, using the previously determined distortion function, ultimately providing sequence files and quality scores in the same format as the standard base-caller.

Figure 9:
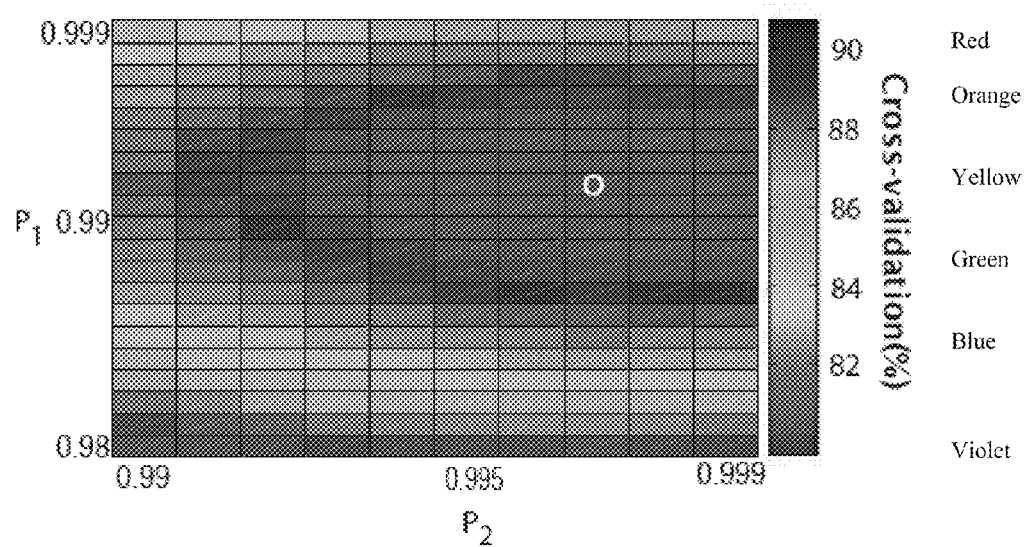
FIG. 9|Grid search for optimization of the random walk de-convolution. The Y-axis corresponds to $P_1$ and the X-axis to $P_2$. The color of each cell indicates the cross-validation rate that was achieved. The white circle shows the values that were chosen (>90% cross-validation).

Alta-Cyclic treats DNA sequencing as a classification problem, where the four analog intensity signals that are generated by detection of the fluorophores should be classified as A, C, G, or T. The training process starts by random sampling of intensity reads from the training library. The intensity reads are matched to their corresponding sequences, and the sequences are aligned to the reference genome, allowing several mismatches. This process generates the training set—fluorescent intensities and their corresponding correct base calls. Alta-Cyclic utilizes an iterative two-dimension grid search to find the best values that describe phasing noise (FIG. 9). In particular, Alta-Cyclic focuses on optimizing the solution for phasing in later cycles, since this data gives better resolution and reflects the overall accumulated noise. Unfortunately, this is somewhat confounded by extensive changes in fluorophore cross-talk. Therefore, at each grid point, Alta-Cyclic first de-convolutes the phasing effect from the intensity values of the training set according to the grid coordinate. Then, it picks the intensity values of the last few cycles and their corresponding correct base calls, and uses an array SVM (Support Vector Machine) to find the optimal margins that separate the fluorophores. Each SVM in the array corresponds to a different cycle. Thus, the number of classification features is 4, as the dimension of the intensity vector. In one embodiment, only half of the training set is used for SVM training and the other half is used for cross-validation. The average success rate in the cross-validation of the SVMs is used as a feedback to the grid search. Hence, in each grid search iteration, Alta-Cyclic converges to more accurate phasing parameters that increase correct classification rates. Following phasing optimization, Alta-Cyclic uses additional grid searches to optimize the SVM learning process by scanning a two-dimensional grid for the SVM cost parameter and gamma kernel parameter, which are hyper parameters for the training process. Alta-Cyclic is then ready for final training of the full array of SVMs (one per cycle), which will be used for base calling. During base calling, intensity files are de-convoluted using the phasing parameters that were found, and resulting intensity values for each cycle are sent for prediction to the corresponding SVM. Alta-Cyclic converts the results to sequences and quality scores, which are based on reported probability of classification from the SVM.

Beside SVM, which provides only discriminative power, other embodiments use a generative model to deconvolute the distortion and decode the sequencing information from the obtained signals. The generative model respecting the Illumina platform includes additional four probability parameters that describe the efficiency of the fluorophore cleavage from each nucleotide. Thus, the model does not infer ad-hoc rules about the cross talk change as in the case of SVM. Instead, it describes the signal by 23 parameters: p1 is a probability for block removal that permits further polymerization in a synthesis cycle, p2 is a probability of incorporation of a blocked nucleotide, p3 is a probability of strand loss, p4A—probability of fluorophore removal from an A nucleotide, p4C—probability of fluorophore removal from a C nucleotide, p4G—probability of fluorophore removal from a G nucleotide, p4T—probability of fluorophore removal from a T nucleotide, and the 16 values of the 4×4 cross talk matrix (see FIG. 12). Inferring these parameters can be performed using different optimization strategies. However a common theme is taking advantage of sequences that were obtained from a library with a known reference, and building an objective function that minimizes the difference (11 or 12 norm) between the model predictions and the actual signals of those sequences. Since the searching space is quite large, an exhaustive grid search may not be applicable as in former random walk model. In one embodiment of this invention, the global minimum, which represents the best tuning of the model parameters respecting the objective function, is approximated by simulated annealing, which is a common optimization method. Similar to the previous embodiment, after the model parameters are inferred, the base-caller enters to the calling stage. The most probable sequence for each signal is defined as the one that when handed to the tuned model gives a predicted signal that is the closest to the observed signal. In order to speed time and memory, in one embodiment of this invention the base caller uses beam-search heuristic to approximate the most probable sequence. The base caller creates a directed tree, where each parent node is connected to 4 daughter nodes that correspond to the four nucleotide possibilities in each cycle. Thus, every path in the tree denotes a possible sequence to consider. The leaf nodes hold the difference between the model prediction and the observed signal according to their path. The beam search restricts the size of the tree, and prunes some of the paths whose leafs have differences that are too large. Hence, only few paths survive and should be processed, and at the end the path with the smallest difference between the prediction and the actual signal is reported. Beside base calling, the generative model has the advantage of simulating sequencing data with typical error profile which is important to determined the feasibility of projects, and the development of downstream applications.

Alta-Cyclic has several notable differences from the standard Illumina base caller. First, all the calling parameters are optimized empirically and tested to enhance the accuracy of the base calling for each run, whereas in the Illumina base caller, parameters are statically derived, and are not evaluated. Second, Alta-Cyclic calculates phasing parameters using data from the latest cycles, which should give better accuracy, whereas the Illumina base caller relies on data from early cycles. Moreover, the Illumina phasing model is based upon a numerical method, whereas phasing description of this invention is based on a parametric model, which can contribute to the accuracy of Alta-Cyclic. Finally, Alta-Cyclic dynamically tracks changes in fluorophore cross talk, which severely disrupts signals in later cycles, whereas the Illumina base caller statically determines cross-talk upon values from early cycles.

Figure 3:
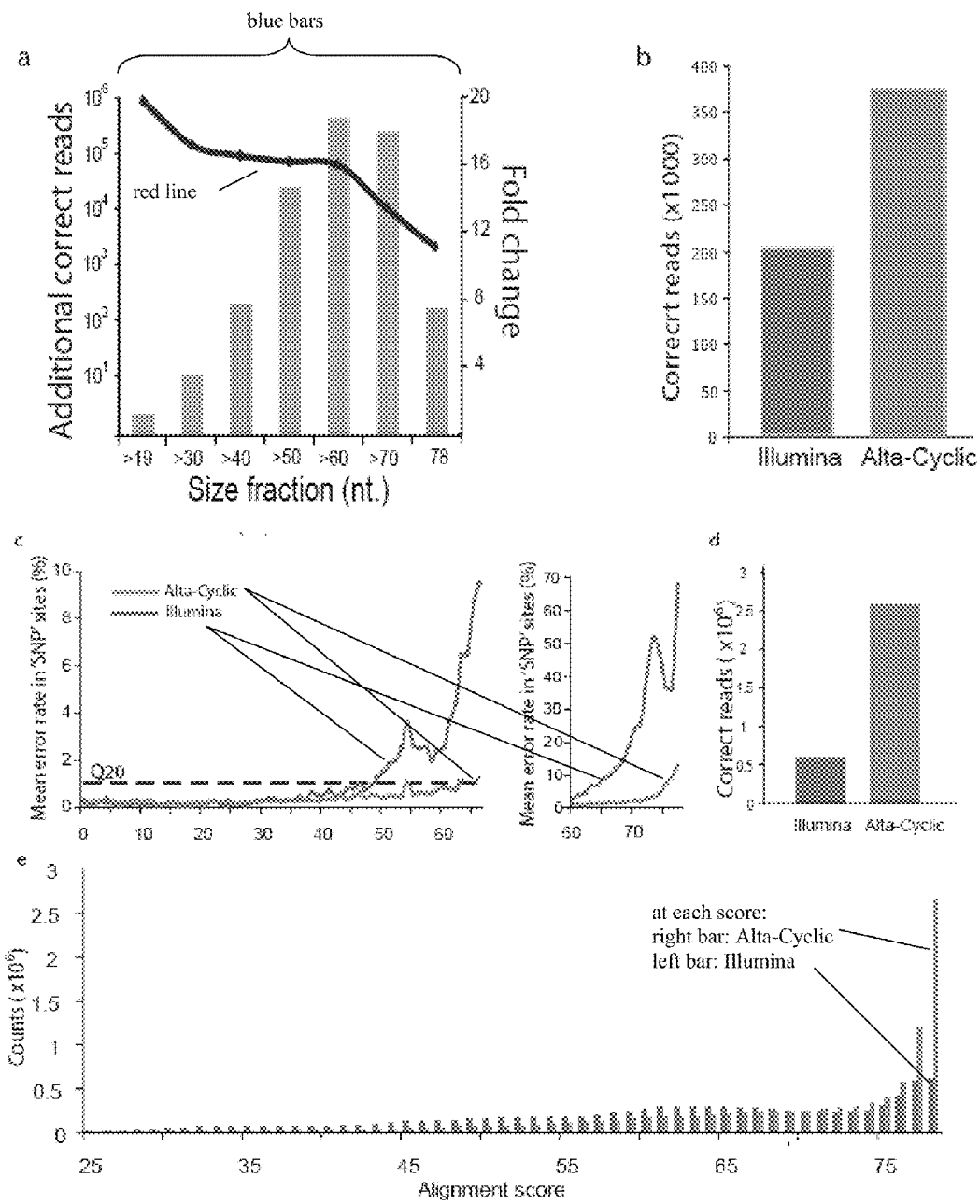
FIG. 3|Comparison between Alta-Cyclic and Illumina base caller on GAII platform. (a) The performance by Alta-Cyclic for the HepG2 RNA library. The absolute number of additional fully correct reads (above those generated by Illumina) is indicated by the red line; the fold change of the improvement is indicated by the blue bars. (b-e) Green represents Alta-Cyclic results, gray represents Illumina base caller results. (b) A comparison between the Illumina base caller and Alta-Cyclic of fully correct reads for the *Tetrahymena* MIC library. (c) The average error rate in calls of the artificial single nucleotide polymorphism SNP locations in the phi-X library as a function of the cycle in which they were called. The span of the Y-axis in the right part of the graph is higher. Alta-Cyclic exhibits remarkably lower error rates than Illumina base caller, particularly for later cycles. It crosses the 1% error rate that corresponds to Q20 only at the $65^{th}$ cycle, 17 cycles after the Illumina base caller. In addition the error profile is the last cycles is significantly lower than the Illumina base caller. This indicates that Alta-Cyclic does not over-fit the data and can use the same intensity data both for training and calling in SNP detection scenario. (d) A comparison between the Illumina base caller and Alta-Cyclic of fully correct reads for the phi-X library with 1% artificial SNPs. (e) phi-X sequences generated by Alta-Cyclic or Illumina were exhaustively aligned to the reference genome (allowing up to 53 mismatches out of 78). The distribution of alignment scores is shown beginning with an identical number of raw reads for input into each base caller.

Alta-Cyclic was tested on both GAI and GAII machines for long runs. On the GAII, test samples were run for 78 cycles. The training set contained 100,000 randomly chosen reads from the phi-X control, which were trimmed to 25 nucleotides, and aligned back to the phi-X genome allowing 5 mismatches. Using the trained program, two human libraries representing small RNAs of <200 bases (see Methods) were based-called. Since these libraries are enriched for miRNAs, known adaptors were clipped and sequences smaller than 19 nucleotides in length were removed. Alta-Cyclic reported about 1,000,000 more fully correct reads than the Illumina base caller after matching to the human genome (FIG. 3a). As a result, the accuracy of longer reads improved most dramatically. Alta-Cyclic improved the number of fully correct >30 base reads by ~3.5× and the number of fully correct reads of >60 bases by 18×. There was also an improvement in adaptor clipping with Alta-Cyclic. With a library of *Tetrahymena* micronuclear DNA, the average improvement for fully correct reads was ~2-fold (FIG. 3b), which was likely reduced in comparison to human samples because of the lack of a reference micronuclear genome and the substantial rearrangement that occurs between the micronuclear DNA and the available reference macronuclear genome[10].

A common hope for next-generation sequencers is the ability to identify sequence variants. For variant calls, sequence data would normally have a reference genome that could be used for training. One caution is that the presence of variants could cause over-fitting of the data or could degrade the accuracy of a learning-based method. To simulate a scenario where there might occur substantial variation between a training set and the actual sequencing target (such as in cross-species comparisons), Alta-Cyclic was re-trained using a phi-X library into which was introduced 1% artificial single-base changes. After training, we base called the phi-X sample and matched the results back to the artificially mutated phi-X genome. We examined the error rate for artificial SNP sites as a function of cycle number after filtering high quality reads (see Methods). Alta-Cyclic called SNPs with <1% error rate in the first 62 cycles, whereas for the Illumina base caller, this error rate was restricted to the first 48 cycles. Furthermore, the mean error rate of SNP calling in the last 10 cycles of Alta-Cyclic was ~5%, while it jumped to 40% for the Illumina base caller (FIG. 3c). When we compared reads to the intact phi-X genome, we found that Alta-Cyclic reported ~2,600,000 correct 78 nt long reads, which represents 22% of all reads. In contrast, the Illumina base caller reported only ~600,000 correct 78 nt long reads, which represents 5% of all reads (FIG. 3d). In addition, we used this model to check whether Alta-Cyclic improves the data globally, even in very noisy reads. We aligned the total Alta-Cyclic and Illumina base caller output to the phi-X genome under highly permissive conditions, allowing up to 53 mismatches in a 78 base run, just slightly above random matching. We found that the average number of mismatches in Alta-Cyclic sequences was 9, whereas it was 16 for the Illumina base caller. This corresponds to more than 100 million additional correct individual base calls in Alta-Cyclic as compared to the Illumina base caller. The distribution of number of mismatches in the library clearly emphasizes that Alta-Cyclic improves even the very noisy reads that would normally be discarded during quality filtering (FIG. 3e). Considering these results together, we conclude that Alta-Cyclic does not over-fit the data in the training process and that the approach enhances overall base calling. Similar improvements were obtained for runs on GAI machines (see Example 2).

The strategies set out in this disclosure both improve the accuracy of base calling and allow the production of longer reads. By extending the accurate read lengths to as much as 78 bases on the GAIL there is a substantial increase potential sequence output. Moreover, longer reads allow more accurate mapping and can allow de novo assembly of complex genomes. Undoubtedly, the hardware underlying next-generation platforms will continue to improve, but it is equally likely that the strategies described here will continue to allow the limits of these platforms to be maximized.

The following examples illustrate the present invention, and are set forth to aid in the understanding of the invention, and should not be construed to limit in any way the scope of the invention as defined in the claims which follow thereafter.

EXAMPLES

Example 1

Creating a Mathematical Model for Solexa Non-stationary Noise Factors

The Illumina GA platform has almost no published literature regarding the exact data processing or the noise factors that are applied or introduced at each stage. Therefore, we started by constructing a comprehensive model describing the signal and non-stationary noise factors. Alta-Cyclic relies on this model, and the training stage is designated to find the best parameters that fit the model to the noise. In the following sections we describe the steps we took in order to develop the present model.

Demonstrating Linearity of the Intensity Values

First, we showed that the intensity values that are generated by the platform are the outcome of a linear transformation to the number of received photons. We checked whether the machine optic channel is linear—that is, that the intensity of the digital .tiff image is linearly correlated with the number transmitted photons. We did this by instructing the sequencer to take images with different exposure times of an intact flow cell to which none of the sequencing chemistry had been applied (Recipe 2). The following exposure times (ms) were used: 1, 25, 50, 75, 100, 125, 150, 200, 250, 300, 350, 400, 600, 800, 1000, 1200, 1400, 1600, 1800, 2000. The captured images were taken from 30 tiles of lane 4, 5 and 7. The median intensity level of every image was determined using the libTiff library and the averaged value from all 30 tiles was calculated. A linear regression of the data found that $r^2$ for all channels was >0.995 (FIG. 4a). Thus, we concluded that the optical channel is linear.

The Illumina analysis pipeline generates intensity files as part of its image analyzer routine, using a program called Firecrest. The intensity files contain the location of each DNA cluster and a measurement of the four signal intensities for each cycle. The reported intensities are not directly derived from the image, but Firecrest applies an image processing step. We checked whether Firecrest applies a linear transformation to the data. We exploited impulse response analysis to study the transfer function of Firecrest. A series of artificial images with spatial "delta functions" of different heights was generated. We send these images to analyze_image software that is part of Firecrest, and we used the command line option 'dump filtered image' and 'object list' option to get back the reported 'intensity'. We found a linear correlation between the input spike and the reported 'intensity' (FIG. 4b). Thus, we can demonstrate that the intensity values are linearly correlated with the number of received photons. This simplifies our mathematical formalization, and allows us to use the intensity flies as input to our base caller.

Impulse Response Analysis as a Tool for Revealing Noise Factors

Impulse response analysis is a common tool in signal processing to characterize distortions in communication channels. The analysis is performed by injection of a sharp pulse, called a delta function, as the input to the system under investigation. The output, measured as a function of time, reflects the system transfer function. The change between the input and output corresponds to the distortion. In sequencing, a delta function corresponds to sequences in which one type of nucleotide dwells in a context of different type of nucleotides. The output is the signal intensities of the corresponding fluorophore as a function of cycle number. For example, the sequences: . . . AAAACAAAA . . . or . . . AGTGCGGTG . . . are both instances of delta functions with respect to the C channel.

Our impulse analysis was largely designated to characterize the properties of phasing. A delta sequence after phasing will have two imperfections. The first is anticipation signal—an increase in the signal intensity in the fluorophore channel corresponds to the delta function during cycles before actual cycle, which corresponds to that nucleotide position. The second is memory signal—persistence of residual signal in the same channel after calling the nucleotide that corresponds to the delta function. Note, that due to the non-stationary nature of this noise factor, we assume the imperfections will escalate in later cycles. To monitor phasing noise, we created 8 delta sequences. We also created two additional types of sequences: dinucleotide microsatellites, and theta function sequences (FIG. 11). Dinucleotide microsatellites, which can also be thought of as a train of delta functions, transmit signal in only two channels that correspond to their alternating constituent bases. Because of the diffusive properties of phasing, the two channels should converge during the run toward half of their initial intensities. The theta function sequences consist of two interleaved short homopolymers—repeats of one nucleotide followed by a repeats of another nucleotide. In total, we synthesized 12 DNA fragments and cloned these as minigenes that contained Illumina sequencing primers and anchors for bridge amplification (see Methods section, below). These were verified by conventional sequencing and excised from their host plasmids prior to loading onto the flow cell. In this way, we avoided any polymerase chain reaction (PCR) amplification step—prior to bridge amplification itself—that could introduce errors. These templates were sequenced for 50 cycles on a GAI.

For analyzing cycle-dependent noise factors, we used the sequence files and the intensity files that are generated by the standard Illumina pipeline. We annotated each cluster. Then, we averaged the signal intensities for DNA cluster with the same annotation. This procedure generated twelve 50-by-4 matrices, in which each row corresponds to a cycle and each column to a fluorophore channel. We found that there is extensive cross-talk between the fluorophore channels, reflecting overlapping emission spectra. Specifically, the fluorophore attached to adenine strongly leaked into the cytosine channel, and signal leaked from the guanine channel to the thymidine channel. Using the delta function sequences, the anticipatory and memory signals, which correspond to phasing, were detected, and these escalated with cycle number (FIG. 5a). Contrary to naïve predictions, the microsatellite sequences did not yield signals that converged to half of their original intensities. Instead, the signals decayed towards zero or faded (FIG. 5b). In fact, after logarithmic transformation the signal intensity showed linear behavior, which implies an exponential decay. Since we could not attribute this effect to phasing, we introduced another noise factor—fading. We found that fading is correlated with the scanning buffer that is used, and switching to the new Illumina scanning buffer decreased the decay rate from ~3% to 1% on the GAI machines. Hence, fading is mainly an outcome of material loss, but we cannot exclude additional mechanisms that might also contribute to fading, such as nascent strand melting or existence of a very small fraction of nucleotides that are irreversibly blocked.

Random Walk Model for Phasing and Fading

Figure 6:
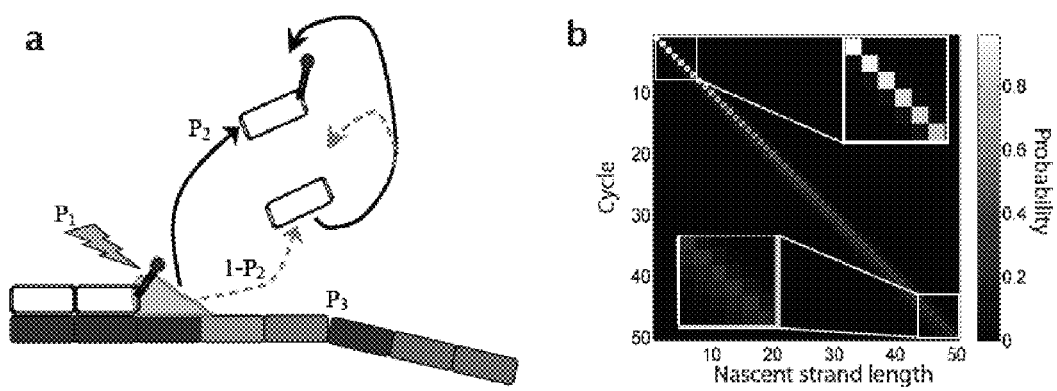
FIG. 6|Random walk model. (a) A schematic illustration of the random walk model is shown. In the initial state the last nucleotide of the nascent DNA strand (white rectangles) is blocked and has a fluorophore label (ball). The block is removed with probability $P_1$, allowing a nucleotide to be incorporated in the next cycle. We assume two types of nucleotides in the mix: blocked and contaminating non-blocked species. A blocked nucleotide is incorporated with probability $P_2$, and the non-blocked with probability $(1-P_2)$. If a non-blocked nucleotide is incorporated the process continues (gray arrows), until a blocked nucleotide is incorporated (black arrows). In addition, the template is lost with $P_3$ probability, due to strand breakage or another processes. (b) Heat map representation of the R matrix calculated by our random walk model with $P_1=0.98$, $P_2=0.99$ and $P_3=0.01$ for 50 cycles. The rows correspond to sequencing cycles and columns to possible nascent strand lengths. The intensity indicates the probability. In an idealized situation, the diagonal would be white and all other cells would be black. Notably, in the first cycles (upper left corner) there is almost no variation in length of the nascent strands, whereas in later cycles (bottom right corner) the variation increases and degrades the correct signal.

We developed a random walk model to describe phasing and fading (FIG. 6a). At the biochemical level, phasing and fading are directly correlated with the nascent strand length. Phasing causes some variation in nascent strand lengths in the DNA cluster, which accumulate throughout the run, and fading exponentially decreases the number of strands in the cluster as a function of cycle. Our random walk model describes the overall effect by three parameters, p1, p2, and p3, with simple probabilistic interpretations. The parameter p1 donates the probability for block removal that permits further polymerization in that cycle. If the block is removed, two mutually exclusive events are considered: (a) incorporation of blocked nucleotide with probability p2, or (b) incorporation of non-blocked nucleotide, which comes from low levels of contamination, with probability of 1−p2. Therefore, in a single cycle the nascent strand stays at the same length without any synthesis with probability 1−p1, grows by a single nucleotide with probability p1×p2, grows by two nucleotides with probability p1×(1−p2)×p2, and so on. The third parameter, p3, donates the probability of strand loss, which leads to signal decay. Note that p1, p2 and p3 are time, cluster-size and sequence invariant, which is a simplification of the real situation. It should be possible to include these effects in a more complete model, but at the cost of increased parametric complexity. The propagator of the random walk model is given by:

$$R(t, n) = e^{-p_3 t} \int_{-\pi}^{\pi} \left[ 1 - p_1 + \frac{p_1 p_2 e^{i\omega}}{1 - (1 - p_2) e^{i\omega}} \right]^t e^{-i\omega n} \frac{d\omega}{2\pi}. \quad (1)$$

Thus, R, is a matrix that gives the probability of a nascent strand to be n nucleotides long after t cycles (FIG. 6b). R can be decomposed to the effect of phasing and fading:

$$D \times P = R. \quad (2)$$

D, the "fading" matrix, is a T-by-T diagonal matrix capturing the exponential decay of the signal, where T is the total number of synthesis cycles. P is a T-by-N matrix that donates the phasing. P(t,n) corresponds to the probability of finding a nascent strand with a length n after t cycles. N is the length of the longest nascent strand, and it cannot be longer than the template length. In the ideal case, D and P would be identity matrices.

The relationship between a DNA sequence a j-th DNA and the received intensities from that cluster is given by:

$$\eta_j \cdot D \times P \times S_j \times G^* = I_j \quad (3)$$

In this model, $\eta_j$ is a scalar that represents the size of the j-th DNA cluster. D and P are the fading and phasing matrices described above. S is an N-by-4 matrix that contains a binary representation of the DNA sequence of the j-th cluster. Each row of S has one element that equals 1 and three elements that equal 0. For instance, the short sequence, 'ACCGT,' would be represented as:

$$S_j = \begin{vmatrix} 1 & 0 & 0 & 0 \\ 0 & 1 & 0 & 0 \\ 0 & 1 & 0 & 0 \\ 0 & 0 & 1 & 0 \\ 0 & 0 & 0 & 1 \end{vmatrix}.$$

G is a 4-by-4 matrix that represents the cross-talk between the channels, and star indicates transposition. In order to maintain the format of this cross-talk matrix as reported by Illumina, each row of G corresponds to the response of the four channels for a fluorophore. Ij donates the intensity signal from the j-th cluster and is a T-by-4 matrix.

In the model described above, one can consider Illumina sequencing as a process that forward transforms the sequence data—nucleotide identity as a function of position—to a fluorophore channel response as a function of cycle number. Therefore, in order to estimate S, the input sequence, an inverse transform must be applied to the intensity matrix. The accuracy of this inverse transform relies heavily on a correct estimation of the phasing and the cross-talk matrices, and is described by:

$$\eta_j \cdot (\hat{P} \times \hat{D})^+ \times D \times P \times S_j \times G^T \times \hat{G}^{T^{-1}} = (\hat{P} \times \hat{D})^+ \times I_j \times \hat{G}^{T^{-1}} \quad (4)$$

In this equation, + represents the pseudo-inverse. If we assign Y as the right hand term of (4), upon correct estimation of the phasing and the cross-talk matrices, (4) can be written as:

$$\eta_j \cdot \Sigma \times S_j = Y \quad (5)$$

where Σ is a band diagonal matrix. The algorithm to find the sequence read is dependent upon the nature of Σ. In a case which the bandwidth of Σ is greater than one, a dynamic algorithm can be applied to find the most likely sequence call[11]. In a case in which Σ is very close to a diagonal matrix, one can find the best sequence call by detecting the strongest signal of Y in each row.

Testing the Parametric Model with a Constant Cross Talk Matrix

We tested the Illumina signal model in (3) using the averaged intensity files generated from our 12 DNA fragments. We obtained an estimation for the cross-talk matrix, G, using the reported values from Illumina. In order to find our experimental parameters we employed a least mean squares fitting procedure, and found that p1 was ~0.98, p2 was ~0.985, and p3, the decay was 3%-5% in each round. We calculated Σ the matrix using these values found that the bandwidth of the matrix was very close to one. Therefore, after de-convolution of phasing, calling a base relies only on the four intensities values that were detected in that specific cycle. Thus, one can normalize the intensities in each cycle, and one does not have to estimate the decay rate. A code that simulates the R matrix (phasing and decay) and Σ upon different p1, p2 and p3, and presents them graphically under HTML, is available.

Figure 7:
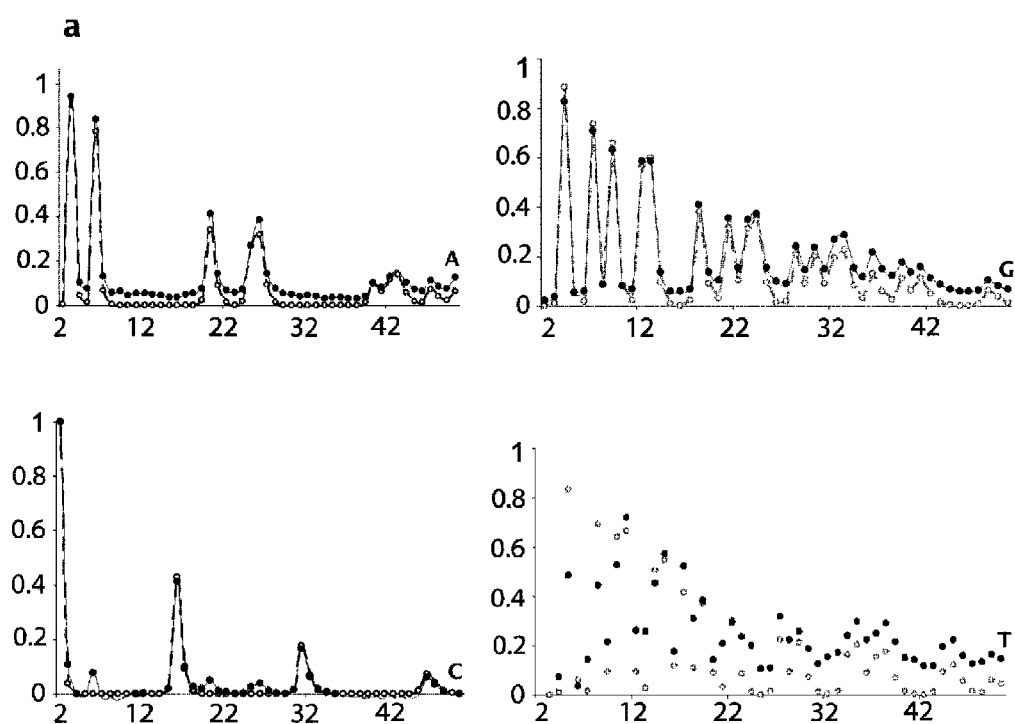
FIG. 7|The model prediction and the anomaly in the T channel. The model prediction (broken lines) is plotted versus the averaged intensity reads (solid lines). The reference data was corrected for fluorophore cross-talk and normalized (A—blue, C—red, G—green, T—purple). (a) Outputs are given for the delta function sequence: GCAGTAGTGTTG-GTTCTGTAGTGGAATGTGCGGTTGTTGAGAATTCA-GTA (SEQ ID NO: 1) (the first cycle is not shown). The reference data was corrected for fluorophore cross-talk and normalized. There is an overall agreement between the model and reference data. Note the T channel anomaly. (b) Shown are the analyses of the theta function sequence: G[7]T[7]G[7]T[7]. . . (SEQ ID NO: 2) (the first cycle is not shown). The intensity of the T channel is very strong in the last cycles where G nucleotides are called. This presumably stems from extensive cross-talk from the G to the T channel. (c) Shown are the analyses of the microsatellite sequence: GTGT . . . (the first cycle is not shown). Again, the T channel intensities are very strong compared to the prediction. The increase in the intensities of the A and C channels around cycle 38 cycle are because of small deletions in the microsatellite sequences that causes some DNA cluster to begin to report the adaptor sequence in that cycle.

In general, we found good agreement between our model and the reference data (FIG. 7a). However, when we closely examined the predictions for the T channels, we found an extensive anomaly. For almost all the sequences in our input set the T channel was stronger than predicted. These deviations were especially strong in the GT microsatellite and the GT theta function sequences (FIGS. 7b,c). We probed the phenomenon more carefully by analyzing sequencing data generated from a phi-X genomic library, which often serves as a control for Illumina sequencing runs. We called phi-X bases according to the P and D matrices that we derived from fitting our model and the cross-talk matrix that is given by Illumina. We found that the overall composition of the called bases changed dramatically as cycle number increased. Specifically, the percentage of T calls increased during late cycles, whereas the percentage of G calls dropped. We observe the same trend with C and A calls, albeit to a lesser extent, with the percentage of C calls increasing and the percentage of A calls decreasing at late cycles. The same trends were observed if we used the standard Illumina base caller rather than our own algorithm (FIG. 8a).

Incorporating Cycle-dependent Cross Talk

The observed deviation from the model was reminiscent of the relationship between the cross-talk in the emissions from G and T and from A and C. We analyzed whether the cross-talk between these fluorescence channels changes over time. The intensity files from the phi-X lane were de-convoluted from the random walk, and the ratios between all the possible 6 pairs of channels were measured. The ratios were normalized using a polar coordinate transformation, binned, and enumerated (FIG. 8b). For instance, signals with a strong C component and a weak T component were presented in the 90 degree bin of the CT histogram, and the opposite instances were presented in the 0 degree bin. The 45-degree line represents the criterion that separates signals from each of the two nucleotides. In the case of accurate cross-talk correction, the two lobes of the histogram should be orthogonal with respect to each other, and close to the axes. Indeed, we found that in early cycles all lobes were orthogonal. In later cycles, the lobe width increased, as expected, due to length spread but the lobes remained orthogonal in most signal pairs. However, the G lobe of the GT histogram underwent a strong shift as cycle number increased. A more subtle shift was noted in the A lobe of the AC histogram. These shifts reflect actual changes in the cross-talk matrix over the course of a run. We therefore revised our model to include a dependency of the cross-talk matrix on cycle number:

$$(\eta_j \cdot D \times P \times S_j) \times G^*(t) = I_j \quad (6)$$

and the inverse model is given by:

$$(\eta_j \cdot (\hat{P} \times \hat{D})^+ \times G^*(t) \times \hat{G}(t)^{*-1} = (\hat{P} \times \hat{D})^+ \times I_j \times \hat{G}(t)^{*-1} \quad (7)$$

Due to extensive variations from run to run and between different machines, the exact description of G as function of cycle is yet to be determined. Thus, we used an SVM in order to address cross-talk changes.

Example 2

Benchmarking Alta-Cyclic on GAI Machines

Figure 10:
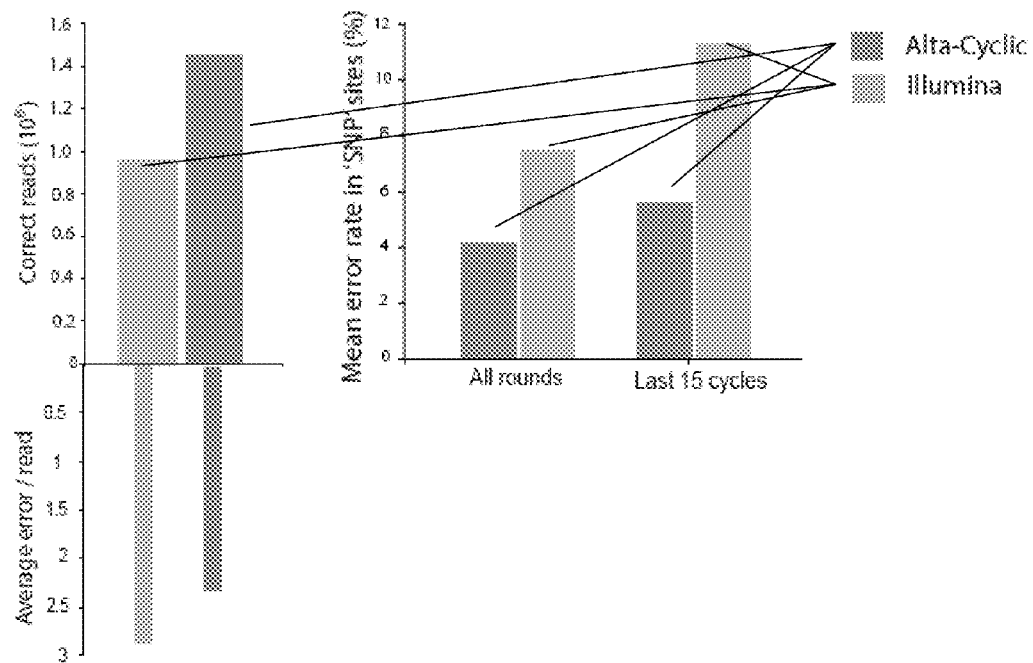
FIG. 10|Comparison between Alta-Cyclic and Illumina base caller on GAI platform. The improvement by Alta-Cyclic for the phi-X library on 50 cycles on GAI. The left graph shows the improvement in the number of fully correct reads and the reduction of the average error rate. The right graph shows a comparison of error rates at the artificial SNP sites between the Illumina base-caller and Alta-Cyclic. The improvement in miscalling is especially noticeable in the later rounds.

We performed an SNP calling experiment on phi-X on the GAI machine using a 50 cycle run. Surprisingly, this yielded similar values for phasing as the GAII run (p1=0.9925, p2=0.9975) (FIG. 9). This may permit us to reduce the area of the grid search and speed training in the future. Overall, Alta-Cyclic increased the number of correct 50 nt reads by a factor of 1.52, reporting ~1,450,000 correct reads, whereas the Illumina base caller reported ~950,000 correct reads. The rate of miscalling SNPs with the Illumina pipeline was around 5.5% across all the cycles; whereas, the Alta-Cyclic miscall rate was 4.1%. The difference in the error rates was elevated for the last 15 cycles. The Illumina base caller missed 11% of the SNPs, but Alta-Cyclic only missed 7% (FIG. 10). Note that these results obtained with the old scanning buffer.

Example 3

Determining the Accuracy of the Generative Random Walk Model

We evaluated the ability of the generative random walk model to predict sequence signals of Illumina GAII run with 101 cycles. As an input to the parameter inferring stage, we sequenced phi-X using 101 cycles, and divided the obtained sequences to two groups—training group, composed of 200 sequence types, and testing group composed of the rest ~10,000 sequence types. We called the sequences the Illumina baseline base-caller as in Example 1. Then, we aligned the sequences of the entire library to the phi-X reference genome allowing mismatches, and we retained the signals that were associated with the training group, and averaged the signals of each sequence type. Using 500 runs of simulated annealing, we searched for the best p1, p2, p3, p4A-T parameters when minimizing l2 norm (we used the cross talk matrix obtained from the Illumina base-caller). The table below shows the searching space and the best value:

| Parameter | Range(%) | Optimal Value(%) |
|---|---|---|
| p1 | 98-100 | 99.36 |
| p2 | 98-100 | 99.12 |
| p3 | 1-5 | 1.18 |
| p4A | 95-100 | 99.62 |
| p4C | 95-100 | 99.62 |
| p4G | 95-100 | 99.14 |
| p4T | 95-100 | 99.61 |

Remarkably, the sequencing data showed a signal build up in the G channel that can be explained by the low value of p4G relative to the other fluorophore cleavage probabilities of the other nucleotides.

Figure 13:
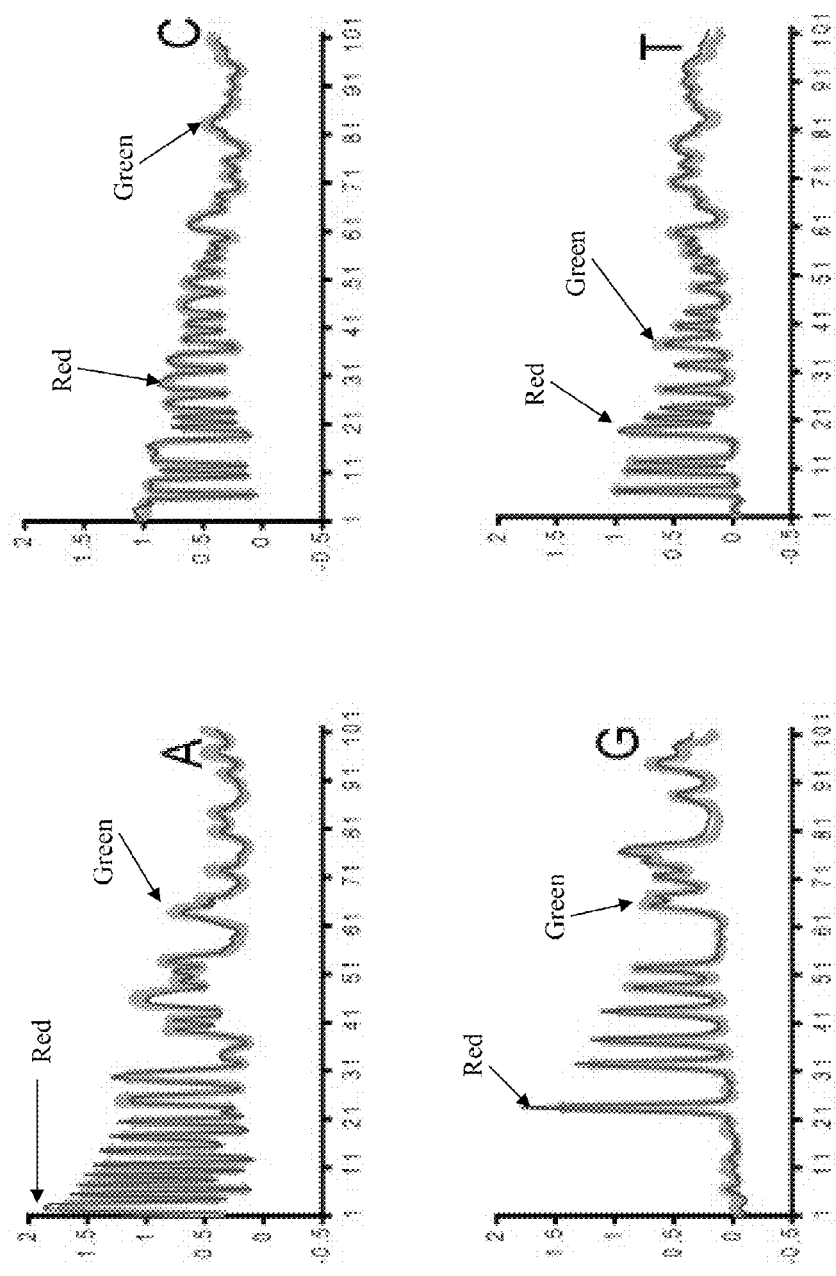
FIG. 13|Results of the Generative Random walk model compared to the averaged signal. The 7 parameters of the random walk model were found using simulated annealing with an objective function that minimizes the squared errors between the actual signals obtained from Phi-X and the corresponding sequences. Then, the model generated signal prediction (thick green line) to sequences that were not part of the training set. These predictions were compared to the actual signal (thin red line). There are striking similarities between the prediction and the actual signal.
Figure 14:
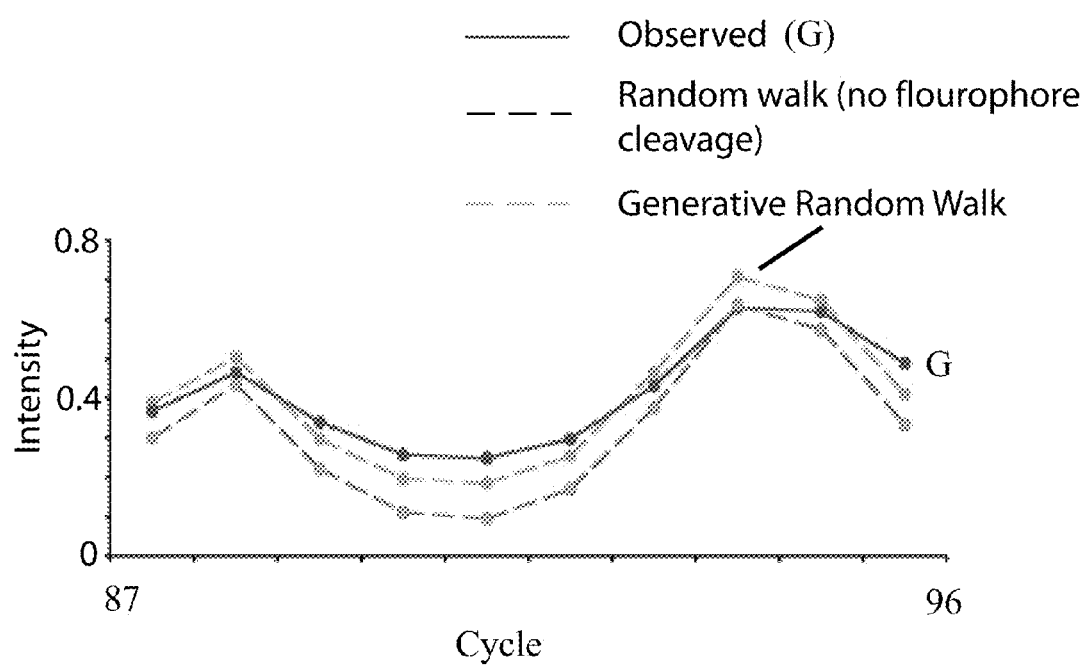
FIG. 14|Comparison between the Generative Random walk to the Random walk with no fluorophore cleavage for the G channel. The signal prediction of the random walk that assume full efficiency in the fluorophore cleavage (FIG. 4) versus the generative model. Both models were tuned using simulated annealing. The actual signal is given as a reference as emphasize the rigor of the generative model. Only the last 16 cycles are shown.

We validated the model by predicting the values of sequences that were not part of the training FIG. 13 shows an example of one of these sequences, and how the model fits the observed data. In addition, we compared the prediction of the random walk model to the generative random walk model. We tuned the random walk by simulated annealing where p4A-T were set to 1 (corresponds to no fluorophore cleavage). FIG. 14 shows a typical example where the generative random model outperforms the random walk one.

Methods

Alta-Cyclic Software

Alta-Cyclic skeleton is written mainly in Perl. It uses BLAT[12] for building the training set, Perl Data Language (PDL)[13] for matrix manipulation, and libSVM[14] for machine learning algorithm. The SVD decomposition is based on Golub-Reinsch algorithm that was implemented using GNU Scientific Library (GSL). The Alta-Cyclic skeleton code and related code are open source. Alta-Cyclic is available at hannonlab.cshl.edu/.

Computer Cluster Architecture

We tested Alta-Cyclic on CSHL's High Performance Computing Cluster (HPCC). The system is an IBM E1350 blade-based cluster running Linux. It comprised 500 compute nodes, but Alta-Cyclic used only ~81 nodes for training, and ~100 nodes for base-calling. Each compute node contained 2 dual-core AMD Opteron™ 64 processors running at 2.0 GHz, a local 73 GB SFF SCSI disk, and memory from 2 to 8 GB. We found that the last SVM training step should be executed on a node with at least 4 GB of memory. Sun Grid Engine (SGE) was used to submit jobs to the compute nodes. The training process took typically 10 hours. Alta-Cyclic requires SGE in order to submit jobs.

Long Runs on Illumina Machines

The 78-cycle GAII run took approximately one week, and additional reagents were added as needed. We modified the machine recipe to run for 80 cycles (Recipe 1). For data storage, we installed a Western-Digital 2Tb external hard-drive using FireWire. However, after 78 cycles the machine stopped the run due to insufficient storage space. Notably, 2Tb is the maximum storage space that is allowed to mount as a single drive on Windows XP, the operating system of Illumina stations. Therefore, any future improvement should also address the storage restriction. The 50-cycle GAI run took approximately 5 days.

Benchmarking and Sample Preparation

The phi-X, HepG2, and Tetrahymena libraries were sequenced on the same flow-cell. The HepG2 (human transcriptome library of the nucleus compartment of HepG2 cells) sample preparation started by isolation of HepG2 nuclei. RNA was extracted with Trizol (Invitrogen) and subsequently small RNA was isolated using the Ambion mirVana kit. 5 μg of small RNA was TAP treated according to manufacturers protocol, but reducing the enzyme to 1 μl. C-tailing was conducted using the Ambion polyA tailing kit, substituting the ATP with CTP. Solexa 5' linker was ligated using Ambion T4 RNA ligase according to manufacturers description. Reverse transcription was conducted with Superscript III according to manufacturers description using the reverse complement of the IDT linked sequence extended by 10 guanine nucleotides. cDNA was amplified, the correct size range (100-300 bp) was gel extracted and submitted for sequencing. Poly-C tail was added to the HepG2 sequences. We trimmed the sequences by finding a block of 'CCCCCC' with up to 2 substitutions. We used Nexalign[15] to find perfect matches to the human genome, and we eliminated matches from sequences with block of 78×T, which is a recurrent sequence artifact on Illumina machines. We collapsed matches from the same sequence to multiple locations, and enumerated the results. This procedure was the same for Illumina base caller and Alta-Cyclic.

For the Tetrahymena sequences (library built from germ-line-like micronucleus (MIC) of Tetrahymena thermophila), we trimmed the first cycle that was additional T nucleotide in the 5' end, and then we extracted the following 60 nucleotides. We aligned the 60 nt long sequence to the Tetrahymena MAC genome to find perfect matches.

The phi-X genome (NC_001422.1) was randomly mutated in about 50 locations, which corresponds to 1% SNPs. After training and calling, BLAT was used to find sequences with less than 4 substitutions to the mutated genome. We filtered reads that are aligned to SNP locations, and extracted the nucleotide identity of these locations, while we also saved the cycle number in which the SNP was called. We compared the SNP identity to the intact genome and calculated the number of errors. For the distribution of number of errors, we used BLAT for alignment with minScore=25, minMatch=1, tileSize=6, minIdentity=25. We filtered the best matches for each read, but we did not include reads that align with gaps.

Generation of Sequences for Impulse Response Analysis

We used miniGene technology (IDT) to synthesize the sequences for testing the impulse response. We synthesized a controlled input set of 12 DNA fragments. The Illumina p5, p7 and SBS3 priming sites were synthesized as part of the fragments and two NlaIII sites flanked each DNA fragment. Each of the four fragment types were cloned into pZero (Invitrogen). We checked the accuracy of clones using conventional ABI sequencing. For Illumina sequencing, the plasmids were cut with 2 μl of NlaIII (NEB), and the 3' prime overhangs were removed with 1 μl of T4 DNA polymerase (NEB). 100-200 bp fragments were selected using 1% agarose gel (Roche) and extracted. The concentration of the DNA from the plasmids was measured and equal amounts were mixed and diluted to 2 ng/μl in TE.

Analysis of the Intensity Files for Impulse Response

Each sequence read of the Illumina sequence files was matched to the 12 possible sequences and the annotation was determined according to the best match. We filtered out sequences with ambiguous base called, represented as a "." in Illumina output. Then, the intensity files were scanned and only DNA clusters in which the intensity values of the first round were stronger than the average passed the filter. We averaged all the intensities according to their annotation. Then, the intensity values for the first cycle were removed, and the strongest point was normalized to 1 and the median of the minimum intensity values from all the cycles was normalized to 0. We used a grid computer to scan different values of $p1$, $p2$ and $p3$ and to extract the sum of the squared error from different types of sequence. We excluded the delta sequences on homopolymer background since we noticed that they were subject to small deletions and insertions, presumably during bridge amplification. These variations could affect the calculation of the random walk parameters.

REFERENCES

1. Pennisi, E. Breakthrough of the year. Human genetic variation. Science 318, 1842-3 (2007).
2. Chi, K. The year of sequencing. Nat Methods 5, 11-4 (2008).
3. Korbel, J. et al. Paired-end mapping reveals extensive structural variation in the human genome. Science 318, 420-6 (2007).
4. Hillier, L. et al. Whole-genome sequencing and variant discovery in C. elegans. Nat Methods 5, 183-8 (2008).

5. Cokus, S. et al. Shotgun bisulphite sequencing of the *Arabidopsis* genome reveals DNA methylation patterning. Nature (2008).
6. Whiteford, N. et al. An analysis of the feasibility of short read sequencing. Nucleic Acids Res. 33, e171 (2005).
7. Chaisson, M. & Pevzner, P. Short read fragment assembly of bacterial genomes. Genome Res 18, 324-30 (2008).
8. Metzker, M. Emerging technologies in DNA sequencing. Genome Res 15, 1767-76 (2005).
9. Metzker, M., Raghavachari, R., Burgess, K. & Gibbs, R. Elimination of residual natural nucleotides from 3'-O-modified-dNTP syntheses by enzymatic mop-up. BioTechniques 25, 814-7 (1998).
10. Eisen, J A. et al. Macronuclear Genome Sequence of the Ciliate *Tetrahymena thermophila*, a Model Eukaryote. PLoS Biol 4(9), e286 (2006).
11. Kailath, T. & Poor, H. V. Detection of stochastic processes. IEEE Transactions on Information Theory, 44, 2230-2231 (1998).
12. Kent, W. BLAT—the BLAST-like alignment tool. Genome Res 12, 656-64 (2002).
13. Glazebrook, K. et al. Perl Data Language. The Perl Journal 5, 5 (1997).
14. Chang, CC. & Lin, C. LIBSVM : a library for support vector machines. Software available at csie.ntu.edu.tw/~cjlin/libsvm (2001).
15. Lassmann, T. et al. Nexalign. Unpublished.

Recipe 1
Recipe for 80 cycles
(Note: the machine will stop after 78 cycles when equipped with a 2Tb storage device)

```xml
<?xml version="1.0" ?>
<RecipeFile>
    <!-- 80Cycle_GA2_v1.xml -->
    <!-- This recipe is for use with the GAII system -->
    <!-- Single Read Recipe -->
    <!-- Exposure Time: Total = 1375 ms (A=500, C=350, G=350, T=175) -->
    <!-- No. Tiles Per Column: 50 -->
    <!-- No. Cycles: 80 -->
    <!-- ImageCyclePump config file should be set to "TRUE" -->
    <!-- Edited by Yaniv Erlich erlich@cshl.edu 4th Apr 2008            -->
    <TileSelection>
        <Incorporation>
            <Lane Index="1"><RowRange Min="1" Max="50"/></Lane>
            <Lane Index="2"><RowRange Min="1" Max="50"/></Lane>
            <Lane Index="3"><RowRange Min="1" Max="50"/></Lane>
            <Lane Index="4"><RowRange Min="1" Max="50"/></Lane>
            <Lane Index="5"><RowRange Min="1" Max="50"/></Lane>
            <Lane Index="6"><RowRange Min="1" Max="50"/></Lane>
            <Lane Index="7"><RowRange Min="1" Max="50"/></Lane>
            <Lane Index="8"><RowRange Min="1" Max="50"/></Lane>
        </Incorporation>
    </TileSelection>
    <ChemistryDefinitions>
        <Chemistry Name="Warning">
            <UserWait   Message="Please Ensure that You have Previously Run the FirstBase Recipe. Press OK to Continue, or CANCEL to Stop." />
        </Chemistry>
        <Chemistry Name="CompleteCycle">
            <PumpToFlowcell Solution="7" AspirationRate="250" DispenseRate="2500" Volume="125" />
            <Temp Temperature="55" Duration="120000" />
            <PumpToFlowcell Solution="6" AspirationRate="250" DispenseRate="2500" Volume="75" />
            <Wait Duration="240000" />
            <PumpToFlowcell Solution="6" AspirationRate="250" DispenseRate="2500" Volume="25" />
            <Wait Duration="240000" />
            <PumpToFlowcell Solution="6" AspirationRate="250" DispenseRate="2500" Volume="25" />
            <Wait Duration="240000" />
            <Temp Temperature="22" Duration="120000" />
            <PumpToFlowcell Solution="5" AspirationRate="250" DispenseRate="2500" Volume="75" />
            <PumpToFlowcell Solution="4" AspirationRate="250" DispenseRate="2500" Volume="75" />
            <PumpToFlowcell Solution="5" AspirationRate="250" DispenseRate="2500" Volume="125" />
            <Temp Temperature="55" Duration="120000" />
            <PumpToFlowcell Solution="1" AspirationRate="250" DispenseRate="2500" Volume="75" />
            <Wait Duration="240000" />
            <PumpToFlowcell Solution="1" AspirationRate="250" DispenseRate="2500" Volume="25" />
            <Wait Duration="240000" />
            <PumpToFlowcell Solution="1" AspirationRate="250" DispenseRate="2500" Volume="25" />
            <Wait Duration="240000" />
            <Temp Temperature="22" Duration="120000" />
            <PumpToFlowcell Solution="5" AspirationRate="250" DispenseRate="2500" Volume="75" />
            <PumpToFlowcell Solution="4" AspirationRate="250" DispenseRate="2500" Volume="75" />
            <PumpToFlowcell Solution="3" AspirationRate="250" DispenseRate="2500" Volume="60" />
            <TempOff />
        </Chemistry>
        <Chemistry Name="End">
            <PumpToFlowcell Solution="2" AspirationRate="250" DispenseRate="2500" Volume="500" />
        </Chemistry>
    </ChemistryDefinitions>
```

Recipe 1
Recipe for 80 cycles
(Note: the machine will stop after 78 cycles when equipped with a 2Tb storage device)

```
<Protocol>
    <ChemistryRef Name="Warning" />
            <!--     Cycle 1     -->
    <Incorporation ExposureA="500" ExposureC="350" ExposureG="350" ExposureT="175" />
            <!--     Cycle 2     -->
    <Incorporation ChemistryName="CompleteCycle" ExposureA="500" ExposureC="350" ExposureG="350" ExposureT="175" />
            <!--     Cycle 3     -->
    <Incorporation ChemistryName="CompleteCycle" ExposureA="500" ExposureC="350" ExposureG="350" ExposureT="175" />
            <!--     Cycle 4     -->
    <Incorporation ChemistryName="CompleteCycle" ExposureA="500" ExposureC="350" ExposureG="350" ExposureT="175" />
            <!--     Cycle 5     -->
    <Incorporation ChemistryName="CompleteCycle" ExposureA="500" ExposureC="350" ExposureG="350" ExposureT="175" />
            <!--     Cycle 6     -->
    <Incorporation ChemistryName="CompleteCycle" ExposureA="500" ExposureC="350" ExposureG="350" ExposureT="175" />
            <!--     Cycle 7     -->
    <Incorporation ChemistryName="CompleteCycle" ExposureA="500" ExposureC="350" ExposureG="350" ExposureT="175" />
            <!--     Cycle 8     -->
    <Incorporation ChemistryName="CompleteCycle" ExposureA="500" ExposureC="350" ExposureG="350" ExposureT="175" />
            <!--     Cycle 9     -->
    <Incorporation ChemistryName="CompleteCycle" ExposureA="500" ExposureC="350" ExposureG="350" ExposureT="175" />
            <!--     Cycle 10    -->
    <Incorporation ChemistryName="CompleteCycle" ExposureA="500" ExposureC="350" ExposureG="350" ExposureT="175" />
            <!--     Cycle 11    -->
    <Incorporation ChemistryName="CompleteCycle" ExposureA="500" ExposureC="350" ExposureG="350" ExposureT="175" />
            <!--     Cycle 12    -->
    <Incorporation ChemistryName="CompleteCycle" ExposureA="500" ExposureC="350" ExposureG="350" ExposureT="175" />
            <!--     Cycle 13    -->
    <Incorporation ChemistryName="CompleteCycle" ExposureA="500" ExposureC="350" ExposureG="350" ExposureT="175" />
            <!--     Cycle 14    -->
    <Incorporation ChemistryName="CompleteCycle" ExposureA="500" ExposureC="350" ExposureG="350" ExposureT="175" />
            <!--     Cycle 15    -->
    <Incorporation ChemistryName="CompleteCycle" ExposureA="500" ExposureC="350" ExposureG="350" ExposureT="175" />
            <!--     Cycle 16    -->
    <Incorporation ChemistryName="CompleteCycle" ExposureA="500" ExposureC="350" ExposureG="350" ExposureT="175" />
            <!--     Cycle 17    -->
    <Incorporation ChemistryName="CompleteCycle" ExposureA="500" ExposureC="350" ExposureG="350" ExposureT="175" />
            <!--     Cycle 18    -->
    <Incorporation ChemistryName="CompleteCycle" ExposureA="500" ExposureC="350" ExposureG="350" ExposureT="175" />
            <!--     Cycle 19    -->
    <Incorporation ChemistryName="CompleteCycle" ExposureA="500" ExposureC="350" ExposureG="350" ExposureT="175" />
            <!--     Cycle 20    -->
    <Incorporation ChemistryName="CompleteCycle" ExposureA="500" ExposureC="350" ExposureG="350" ExposureT="175" />
            <!--     Cycle 21    -->
    <Incorporation ChemistryName="CompleteCycle" ExposureA="500" ExposureC="350" ExposureG="350" ExposureT="175" />
            <!--     Cycle 22    -->
    <Incorporation ChemistryName="CompleteCycle" ExposureA="500" ExposureC="350" ExposureG="350" ExposureT="175" />
            <!--     Cycle 23    -->
    <Incorporation ChemistryName="CompleteCycle" ExposureA="500" ExposureC="350" ExposureG="350" ExposureT="175" />
            <!--     Cycle 24    -->
    <Incorporation ChemistryName="CompleteCycle" ExposureA="500" ExposureC="350" ExposureG="350" ExposureT="175" />
            <!--     Cycle 25    -->
```

-continued

Recipe 1
Recipe for 80 cycles
(Note: the machine will stop after 78 cycles when equipped with a 2Tb storage device)

```
        <Incorporation ChemistryName="CompleteCycle" ExposureA="500" ExposureC="350" ExposureG="350" ExposureT="175" />
                <!--    Cycle 26    -->
        <Incorporation ChemistryName="CompleteCycle" ExposureA="500" ExposureC="350" ExposureG="350" ExposureT="175" />
                <!--    Cycle 27    -->
        <Incorporation ChemistryName="CompleteCycle" ExposureA="500" ExposureC="350" ExposureG="350" ExposureT="175" />
                <!--    Cycle 28    -->
        <Incorporation ChemistryName="CompleteCycle" ExposureA="500" ExposureC="350" ExposureG="350" ExposureT="175" />
                <!--    Cycle 29    -->
        <Incorporation ChemistryName="CompleteCycle" ExposureA="500" ExposureC="350" ExposureG="350" ExposureT="175" />
                <!--    Cycle 30    -->
        <Incorporation ChemistryName="CompleteCycle" ExposureA="500" ExposureC="350" ExposureG="350" ExposureT="175" />
                <!--    Cycle 31    -->
        <Incorporation ChemistryName="CompleteCycle" ExposureA="500" ExposureC="350" ExposureG="350" ExposureT="175" />
                <!--    Cycle 32    -->
        <Incorporation ChemistryName="CompleteCycle" ExposureA="500" ExposureC="350" ExposureG="350" ExposureT="175" />
                <!--    Cycle 33    -->
        <Incorporation ChemistryName="CompleteCycle" ExposureA="500" ExposureC="350" ExposureG="350" ExposureT="175" />
                <!--    Cycle 34    -->
        <Incorporation ChemistryName="CompleteCycle" ExposureA="500" ExposureC="350" ExposureG="350" ExposureT="175" />
                <!--    Cycle 35    -->
        <Incorporation ChemistryName="CompleteCycle" ExposureA="500" ExposureC="350" ExposureG="350" ExposureT="175" />
                <!--    Cycle 36    -->
        <Incorporation ChemistryName="CompleteCycle" ExposureA="500" ExposureC="350" ExposureG="350" ExposureT="175" />
                <!--    Cycle 37    -->
        <Incorporation ChemistryName="CompleteCycle" ExposureA="500" ExposureC="350" ExposureG="350" ExposureT="175" />
                <!--    Cycle 38    -->
        <Incorporation ChemistryName="CompleteCycle" ExposureA="500" ExposureC="350" ExposureG="350" ExposureT="175" />
                <!--    Cycle 39    -->
        <Incorporation ChemistryName="CompleteCycle" ExposureA="500" ExposureC="350" ExposureG="350" ExposureT="175" />
                <!--    Cycle 40    -->
        <Incorporation ChemistryName="CompleteCycle" ExposureA="500" ExposureC="350" ExposureG="350" ExposureT="175" />
                <!--    Cycle 41    -->
        <Incorporation ChemistryName="CompleteCycle" ExposureA="500" ExposureC="350" ExposureG="350" ExposureT="175" />
                <!--    Cycle 42    -->
        <Incorporation ChemistryName="CompleteCycle" ExposureA="500" ExposureC="350" ExposureG="350" ExposureT="175" />
                <!--    Cycle 43    -->
        <Incorporation ChemistryName="CompleteCycle" ExposureA="500" ExposureC="350" ExposureG="350" ExposureT="175" />
                <!--    Cycle 44    -->
        <Incorporation ChemistryName="CompleteCycle" ExposureA="500" ExposureC="350" ExposureG="350" ExposureT="175" />
                <!--    Cycle 45    -->
        <Incorporation ChemistryName="CompleteCycle" ExposureA="500" ExposureC="350" ExposureG="350" ExposureT="175" />
                <!--    Cycle 46    -->
        <Incorporation ChemistryName="CompleteCycle" ExposureA="500" ExposureC="350" ExposureG="350" ExposureT="175" />
                <!--    Cycle 47    -->
        <Incorporation ChemistryName="CompleteCycle" ExposureA="500" ExposureC="350" ExposureG="350" ExposureT="175" />
                <!--    Cycle 48    -->
        <Incorporation ChemistryName="CompleteCycle" ExposureA="500" ExposureC="350" ExposureG="350" ExposureT="175" />
                <!--    Cycle 49    -->
        <Incorporation ChemistryName="CompleteCycle" ExposureA="500" ExposureC="350" ExposureG="350" ExposureT="175" />
                <!--    Cycle 50    -->
```

| Recipe 1 |
| --- |
| Recipe for 80 cycles |
| (Note: the machine will stop after 78 cycles when equipped with a 2Tb storage device) |

```
<Incorporation ChemistryName="CompleteCycle" ExposureA="500" ExposureC="350" ExposureG="350" ExposureT="175" />
                <!--     Cycle 51      -->
<Incorporation ChemistryName="CompleteCycle" ExposureA="500" ExposureC="350" ExposureG="350" ExposureT="175" />
                <!--     Cycle 52      -->
<Incorporation ChemistryName="CompleteCycle" ExposureA="500" ExposureC="350" ExposureG="350" ExposureT="175" />
                <!--     Cycle 53      -->
<Incorporation ChemistryName="CompleteCycle" ExposureA="500" ExposureC="350" ExposureG="350" ExposureT="175" />
                <!--     Cycle 54      -->
<Incorporation ChemistryName="CompleteCycle" ExposureA="500" ExposureC="350" ExposureG="350" ExposureT="175" />
                <!--     Cycle 55      -->
<Incorporation ChemistryName="CompleteCycle" ExposureA="500" ExposureC="350" ExposureG="350" ExposureT="175" />
                <!--     Cycle 56      -->
<Incorporation ChemistryName="CompleteCycle" ExposureA="500" ExposureC="350" ExposureG="350" ExposureT="175" />
                <!--     Cycle 57      -->
<Incorporation ChemistryName="CompleteCycle" ExposureA="500" ExposureC="350" ExposureG="350" ExposureT="175" />
                <!--     Cycle 58      -->
<Incorporation ChemistryName="CompleteCycle" ExposureA="500" ExposureC="350" ExposureG="350" ExposureT="175" />
                <!--     Cycle 59      -->
<Incorporation ChemistryName="CompleteCycle" ExposureA="500" ExposureC="350" ExposureG="350" ExposureT="175" />
                <!--     Cycle 60      -->
<Incorporation ChemistryName="CompleteCycle" ExposureA="500" ExposureC="350" ExposureG="350" ExposureT="175" />
                <!--     Cycle 61      -->
<Incorporation ChemistryName="CompleteCycle" ExposureA="500" ExposureC="350" ExposureG="350" ExposureT="175" />
                <!--     Cycle 62      -->
<Incorporation ChemistryName="CompleteCycle" ExposureA="500" ExposureC="350" ExposureG="350" ExposureT="175" />
                <!--     Cycle 63      -->
<Incorporation ChemistryName="CompleteCycle" ExposureA="500" ExposureC="350" ExposureG="350" ExposureT="175" />
                <!--     Cycle 64      -->
<Incorporation ChemistryName="CompleteCycle" ExposureA="500" ExposureC="350" ExposureG="350" ExposureT="175" />
                <!--     Cycle 65      -->
<Incorporation ChemistryName="CompleteCycle" ExposureA="500" ExposureC="350" ExposureG="350" ExposureT="175" />
                <!--     Cycle 66      -->
<Incorporation ChemistryName="CompleteCycle" ExposureA="500" ExposureC="350" ExposureG="350" ExposureT="175" />
                <!--     Cycle 67      -->
<Incorporation ChemistryName="CompleteCycle" ExposureA="500" ExposureC="350" ExposureG="350" ExposureT="175" />
                <!--     Cycle 68      -->
<Incorporation ChemistryName="CompleteCycle" ExposureA="500" ExposureC="350" ExposureG="350" ExposureT="175" />
                <!--     Cycle 69      -->
<Incorporation ChemistryName="CompleteCycle" ExposureA="500" ExposureC="350" ExposureG="350" ExposureT="175" />
                <!--     Cycle 70      -->
<Incorporation ChemistryName="CompleteCycle" ExposureA="500" ExposureC="350" ExposureG="350" ExposureT="175" />
                <!--     Cycle 71      -->
<Incorporation ChemistryName="CompleteCycle" ExposureA="500" ExposureC="350" ExposureG="350" ExposureT="175" />
                <!--     Cycle 72      -->
<Incorporation ChemistryName="CompleteCycle" ExposureA="500" ExposureC="350" ExposureG="350" ExposureT="175" />
                <!--     Cycle 73      -->
<Incorporation ChemistryName="CompleteCycle" ExposureA="500" ExposureC="350" ExposureG="350" ExposureT="175" />
                <!--     Cycle 74      -->
<Incorporation ChemistryName="CompleteCycle" ExposureA="500" ExposureC="350" ExposureG="350" ExposureT="175" />
                <!--     Cycle 75      -->
```

Recipe 1
Recipe for 80 cycles
(Note: the machine will stop after 78 cycles when equipped with a 2Tb storage device)

```
    <Incorporation ChemistryName="CompleteCycle" ExposureA="500" ExposureC="350" ExposureG="350" ExposureT="175" />
            <!--    Cycle 76    -->
    <Incorporation ChemistryName="CompleteCycle" ExposureA="500" ExposureC="350" ExposureG="350" ExposureT="175" />
            <!--    Cycle 77    -->
    <Incorporation ChemistryName="CompleteCycle" ExposureA="500" ExposureC="350" ExposureG="350" ExposureT="175" />
            <!--    Cycle 78    -->
    <Incorporation ChemistryName="CompleteCycle" ExposureA="500" ExposureC="350" ExposureG="350" ExposureT="175" />
            <!--    Cycle 79    -->
    <Incorporation ChemistryName="CompleteCycle" ExposureA="500" ExposureC="350" ExposureG="350" ExposureT="175" />
            <!--    Cycle 80    -->
    <Incorporation ChemistryName="CompleteCycle" ExposureA="500" ExposureC="350" ExposureG="350" ExposureT="175" />
    <ChemistryRef Name="End" />
  </Protocol>
</RecipeFile>
--- end of recipe ---
```

Recipe 2
Recipe for taking images with different exposure time

```
<?xml version="1.0" ?>
<RecipeFile>
        <!-- 36Cycle_v1.xml -->
        <!-- Service protocol made by Yaniv Erlich 12/19/07 -->
        <!-- Exposure time: variable -->
        <!-- No. tiles per column: 15 -->
        <!-- No. Cycles: No Chemistrey -->
    <TileSelection>
        <Incorporation>
            <Lane Index="4"><RowRange Min="1" Max="15"/></Lane>
            <Lane Index="5"><RowRange Min="1" Max="15"/></Lane>
            <Lane Index="7"><RowRange Min="1" Max="15"/></Lane>
        </Incorporation>
    </TileSelection>
    <ChemistryDefinitions>
    </ChemistryDefinitions>
    <Protocol>
                <!--    Going from smaller to bigger to avoid bleaching    -->
        <Incorporation ExposureA="1" ExposureC="1" ExposureG="1" ExposureT="1" />
            <Wait Duration="120000" />
        <Incorporation ExposureA="25" ExposureC="25" ExposureG="25" ExposureT="25" />
            <Wait Duration="120000" />
        <Incorporation ExposureA="50" ExposureC="50" ExposureG="50" ExposureT="50" />
            <Wait Duration="120000" />
        <Incorporation ExposureA="75" ExposureC="75" ExposureG="75" ExposureT="75" />
            <Wait Duration="120000" />
        <Incorporation ExposureA="100" ExposureC="100" ExposureG="100" ExposureT="100" />
            <Wait Duration="120000" />
        <Incorporation ExposureA="125" ExposureC="125" ExposureG="125" ExposureT="125" />
            <Wait Duration="120000" />
        <Incorporation ExposureA="150" ExposureC="150" ExposureG="150" ExposureT="150" />
            <Wait Duration="120000" />
        <Incorporation ExposureA="200" ExposureC="200" ExposureG="200" ExposureT="200" />
            <Wait Duration="120000" />
        <Incorporation ExposureA="250" ExposureC="250" ExposureG="250" ExposureT="250" />
            <Wait Duration="120000" />
        <Incorporation ExposureA="300" ExposureC="300" ExposureG="300" ExposureT="300" />
            <Wait Duration="120000" />
        <Incorporation ExposureA="350" ExposureC="350" ExposureG="350" ExposureT="350" />
            <Wait Duration="120000" />
        <Incorporation ExposureA="400" ExposureC="400" ExposureG="400" ExposureT="400" />
            <Wait Duration="120000" />
        <Incorporation ExposureA="600" ExposureC="600" ExposureG="600" ExposureT="600" />
            <Wait Duration="120000" />
        <Incorporation ExposureA="800" ExposureC="800" ExposureG="800" ExposureT="800" />
            <Wait Duration="120000" />
```

| Recipe 2 |
| --- |
| Recipe for taking images with different exposure time |

```
    <Incorporation ExposureA="1000" ExposureC="1000" ExposureG="1000" ExposureT="1000" />
        <Wait Duration="120000" />
    <Incorporation ExposureA="1200" ExposureC="1200" ExposureG="1200" ExposureT="1200" />
        <Wait Duration="120000" />
    <Incorporation ExposureA="1400" ExposureC="1400" ExposureG="1400" ExposureT="1400" />
        <Wait Duration="120000" />
    <Incorporation ExposureA="1600" ExposureC="1600" ExposureG="1600" ExposureT="1600" />
        <Wait Duration="120000" />
    <Incorporation ExposureA="1800" ExposureC="1800" ExposureG="1800" ExposureT="1800" />
        <Wait Duration="120000" />
    <Incorporation ExposureA="2000" ExposureC="2000" ExposureG="2000" ExposureT="2000" />
  </Protocol>
</RecipeFile>
--- end of recipe ---
```

We claim:

1. A computer-implemented method of DNA sequencing, the method comprising:
    (a) providing a training library of DNA fragments, the DNA sequence of each fragment in the training library being substantially known;
    (b) providing a DNA sample to be sequenced;
    (c) measuring in parallel a first signal and a second signal, the first signal corresponding to a nucleotide in the DNA fragments from the training library, the second signal corresponding to a nucleotide in the DNA sample;
    (d) determining a distortion function, the distortion function representing a difference between the first signal and an expected value of the first signal, the expected value of the first signal being based on the training library; and
    (e) applying the distortion function to the second signal to generate the sequence of the DNA sample.

2. The method of claim 1, wherein the training library comprises at least about 100 DNA fragments.

3. The method of claim 1, wherein the training library comprises at least about 1000 DNA fragments.

4. The method of claim 1, wherein the training library comprises at least about 10,000 DNA fragments.

5. The method of claim 1, wherein the distortion function is determined by a learning machine.

6. The method of claim 5, wherein the learning machine is a support vector machine.

7. The method of claim 6 comprising cross-validating the learning machine using a second fraction of the training library.

8. The method of claim 7, wherein the distortion function comprises a parameter representing a source of noise in the sequencer.

9. The method of claim 8, further comprising performing a grid search for the at least one parameter describing a source of noise in the sequencer using results of the cross-validating.

10. The method of claim 1, wherein the DNA sequencing is by synthesis, and wherein the first signal and the expected value of the first signal are calculated using a parametric model given by:

$$R(t, n) = e^{-p_3 t} \int_{-\pi}^{\pi} \left[ 1 - p_1 + \frac{p_1 p_2 e^{i\omega}}{1 - (1 - p_2)e^{i\omega}} \right]^t e^{-i\omega n} \frac{d\omega}{2\pi}$$

wherein
p1 is a probability for block removal that permits further polymerization in a synthesis cycle,
p2 is a probability of incorporation of a blocked nucleotide,
p3 is a probability of strand loss,
R is a matrix representing a probability of a nascent strand to be n nucleotides long after t cycles,
D×P=R,
D is a T-by-T diagonal matrix representing exponential decay of the signal, where T is a total number of synthesis cycles,
P is a T-by-N matrix representing phasing, where P(t,n) corresponds to a probability of finding a nascent strand with a length n after t synthesis cycles, and
N is a length of the longest nascent strand, and cannot be greater than the template length.

11. The method of claim 10, further comprising determining p1 and p2 using a first grid search.

12. The method of claim 11, further comprising determining optimal learning machine parameters using a second grid search.

13. The method of claim 12, wherein a signal I from a j-th DNA cluster ($I_j$) is given by:

$$(\eta_j \cdot D \times P \times S_j) \times G^*(t) = I_j$$

wherein $\eta_j$ is a scalar that represents a size of the j-th DNA cluster,

D is a T-by-T diagonal matrix representing exponential decay of the signal, where T is a total number of synthesis cycles, P is a T-by-N matrix representing phasing, where P(t,n) corresponds to a probability of finding a nascent strand with a length n after t synthesis cycles, N is a length of the longest nascent strand, and cannot be greater than the template length, $S_j$ is an N-by-4 matrix that contains a binary representation of the DNA sequence of the j-th DNA cluster, G is 4-by-4 matrix that represents cross-talk between channels and is dependent on cycle number,

* indicates transposition, and $I_j$ represents the signal from the j-th cluster and is a T-by-4 matrix.

14. The method of claim 11, further comprising:

deconvoluting the at least one signal using p1 and p2 determined from the first grid search, wherein the deconvoluting comprises performing an inverse transformation given by:

$$(\theta_j \cdot (\hat{P} \times \hat{D})^+ \times D \times P \times S_j) \times G^*(t) \times \hat{G}(t)^{*-1} = (\hat{P} \times \hat{D})^+ \times I_j \times \hat{G}(t)^{*-1}$$

wherein

+ represents pseudo-inverse, $\theta_j \cdot \Sigma \times S_j = Y$, wherein Y is the right hand part of the inverse transformation equation and $\Sigma$ is a band diagonal matrix, D is a T-by-T diagonal matrix representing exponential decay of the signal, where T is a total number of synthesis cycles, P is a T-by-N matrix representing phasing, where P(t,n) corresponds to a probability of finding a nascent strand with a length n after t synthesis cycles, N is a length of the longest nascent strand, and cannot be greater than the template length, $S_j$ is an N-by-4 matrix that contains a binary representation of the DNA sequence of the j-th DNA cluster, G is 4-by-4 matrix that represents cross-talk between channels and is dependent on cycle number,

* indicates transposition, and $I_j$ represents the signal from the j-th cluster and is a T-by-4 matrix.

15. The method of claim 1, wherein the DNA fragments are from a known genome.

16. The method of claim 1, wherein the DNA fragments comprise artificially created sequences.

17. The method of claim 1, wherein applying the distortion function comprises deconvoluting the second signal.

18. A computer-implemented method of enhancing DNA sequencing outcomes, the method comprising:

a) measuring at least one signal that corresponds to a nucleotide in a DNA sample to be sequenced;

b) determining at least one sequence for the DNA sample using the at least one signal and a correction for cross-talk noise in the at least one signal, wherein the correction for cross-talk noise is dependent on a synthesis cycle number;

c) inferring parameters that describe the at least one signal by optimizing an objective function that is built upon known exemplars; and d) using the inferred parameters to reduce noise and distortion in the at least one signal, thereby enhancing DNA sequencing outcomes.

19. The system of claim 18, wherein the optimizing is by beam search.

20. The system of claim 18, wherein the optimizing is by branch and bound.

21. The system of claim 18, wherein the optimizing is by exhaustive search.

22. The system of claim 18, wherein the optimizing is by semi-definite programming.

23. The system of claim 18, wherein the optimizing is by simulated annealing.

24. A computer-implemented method of DNA sequencing by synthesis, the method comprising:

a) measuring at least one signal that corresponds to a nucleotide in a DNA sample to be sequenced;

b) deconvoluting the at least one signal by an inverse transformation given by:

$$(\eta_j \cdot (\hat{P} \times \hat{D})^+ \times D \times P \times S_j) \times G^*(t) \times G^*(t) \times \hat{G}(t)^{*-1} = (\hat{P} \times \hat{D})^+ \times I_j \times \hat{G}(t)^{*-1}$$

+ represents pseudo-inverse, $\eta_j \cdot \Sigma \times S_j = Y$, wherein Y is the right hand part of the inverse transformation equation and $\Sigma$ is a band diagonal matrix, D is a T-by-T diagonal matrix representing exponential decay of the signal, where T is a total number of synthesis cycles, P is a T-by-N matrix representing phasing, where P(t,n) corresponds to a probability of finding a nascent strand with a length n after t synthesis cycles, N is a length of the longest nascent strand, and cannot be greater than the template length, $S_j$ is an N-by-4 matrix that contains a binary representation of the DNA sequence of the j-th DNA cluster, G is 4-by-4 matrix that represents cross-talk between channels and is dependent on cycle number,

* indicates transposition, and $I_j$ represents the signal from the j-th cluster and is a T-by-4 matrix; and c) determining at least one sequence for the DNA sample using the deconvoluted signal.

25. A system for DNA sequencing, the system comprising:

(i) a training library of DNA fragments, the DNA sequence of each fragment in the training library being substantially known;

(ii) a DNA sample to be sequenced, wherein the DNA sample comprises DNA molecules;

(iii) a first signal and a second signal, measured in parallel, the first signal corresponding to a nucleotide in the DNA fragments from the training library, the second signal corresponding to a nucleotide in the DNA sample; and (iv) logic, stored in a computer readable medium, configured (1) to determine a distortion function, the distortion function representing a difference between the first signal and an expected value of the first signal, the expected value of the first signal being based on the training library; and (2) to apply the distortion function to the second signal to generate the sequence of the DNA sample.

26. The system of claim 25, wherein the logic is configured to deconvolute the signal.

27. The system of claim 25, wherein the training library comprises at least about 100 DNA fragments.

28. The system of claim 25, wherein the training library comprises at least about 1000 DNA fragments.

29. The system of claim 25, wherein the training library comprises at least about 10,000 DNA fragments.

30. The system of claim 25, wherein the DNA sequencing is by synthesis, and wherein the logic is based on a parametric model given by:

$$R(t, n) = e^{-p_3 t} \int_{-\pi}^{\pi} \left[ 1 - p_1 + \frac{p_1 p_2 e^{i\omega}}{1 - (1 - p_2)e^{i\omega}} \right]^t e^{-i\omega n} \frac{d\omega}{2\pi}$$

wherein
p1 is a probability for block removal that permits further polymerization in a synthesis cycle,
p2 is a probability of incorporation of a blocked nucleotide,
p3 is a probability of strand loss,
R is a matrix representing a probability of a nascent strand to be n nucleotides long after t cycles,
D×P=R,
D is a T-by-T diagonal matrix representing exponential decay of the signal, where T is a total number of synthesis cycles,
P is a T-by-N matrix representing phasing, where P(t,n) corresponds to a probability of finding a nascent strand with a length n after t synthesis cycles, and
N is a length of the longest nascent strand, and cannot be greater than the template length.

31. The system of claim 25, wherein the plurality of DNA fragments are from a known genome.

32. The system of claim 25, wherein the DNA fragments comprise artificially created sequences.

33. A system for generating a training set to be used in DNA sequencing, the system comprising:
   i) a DNA sample to be analyzed, wherein at least one signal is generated from the DNA sample;
   ii) a training library, wherein the training library comprises a plurality of DNA fragments, and their known sequences stored in a computer readable medium, and at least one signal generated from the DNA sample that corresponds to a nucleotide in the training library DNA; and
   iii) logic comprising a set of instructions stored in a computer readable medium and configured to determine at least one sequence for the training library DNA fragments using the at least one signal and a standard base caller and align the at least one sequence for the training library DNA to its known sequence, thus generating a training set comprising at least one signal measured for the training library DNA and its corresponding correct nucleotide.

34. A computer-implemented method for generating a training set to be used in DNA sequencing, the method comprising:
   a) providing a training library, wherein the training library comprises a plurality of DNA fragments, and their known sequences stored in a computer readable medium;
   b) measuring at least one signal in a DNA sample to be analyzed, wherein the at least one signal corresponds to a nucleotide in the training library DNA;
   c) determining at least one sequence for the training library DNA using the at least one signal and a standard base caller;
   d) aligning the at least one sequence for the training library DNA to its known sequence, thus generating a training set comprising at least one signal measured for the training library DNA and its corresponding correct nucleotide.

35. A computer-implemented method of DNA sequencing, the method comprising:
   (a) providing a training library of DNA fragments, the DNA sequence of each fragment in the training library being substantially known;
   (b) generating a set of expected signals, each of the expected signals representing an output expected to be generated by a DNA sequencer when a fragment in the training library is applied to the DNA sequencer;
   (c) providing a DNA sample to be sequenced;
   (d) applying the DNA sample and at least some fragments from the training library to the DNA sequencer, the DNA sequencer generating a first signal and one or more control signals, the first signal being indicative of the DNA sequence of the sample, each of the control signals being indicative of the DNA sequence of one of the at least some fragments from the training library;
   (e) determining a distortion function, the distortion function representing a difference between at least some of the control signals and at least some of the expected signals;
   (f) applying the distortion function to the first signal to generate an output signal representative of the sequence of the DNA sample.

* * * * *

SEQUENCE LISTING

<160> NUMBER OF SEQ ID NOS: 13

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcagtagtgt tggttctgta gtggaatgtg cggttgttga gaattcagta          50

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 ggggggttt ttttggggg gtttttt                                     28

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cagtcggccg tcggtatcct ggtggtggct aggctgtctc tttccacggc          50

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cgccttacaa ttcaaagtcc atataacttt gaataacctt acatcgatat          50

```
<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctagccgcga caacatagca ggcacgagag tcgacggaca gcggatgcga           50

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
acaaaaaaaa aaacaaaaa aaaaaaaac aaaaaaaaaa aaaacaaaaa             50

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agaaaaaaaa aaagaaaaa aaaaaaaag aaaaaaaaaa aaagaaaaa              50

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8 tcttttttt ttttctttt ttttttttc tttttttttt ttttcttttt              50

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9 tgttttttt ttttgttttt tttttttttg tttttttttt ttttgttttt            50

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
acacacacac acacacacac acacacacac acacattg                       38
```

```
<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtgtgtgtgt gtgtgtgtgt gtgtgtgtgt gtgtgcca                              38

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaaaaaaccc ccccaaaaaa accccccaa aaaaaccc                               38

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 ggggggttt ttttgggggg gtttttttgg ggggttt                                38
```